(12) United States Patent
Lizasoain Hernandez et al.

(10) Patent No.: US 10,808,252 B2
(45) Date of Patent: *Oct. 20, 2020

(54) APTAMERS SPECIFIC FOR TLR-4 AND USES THEREOF

(71) Applicant: APTATARGETS, S.L., Madrid (ES)

(72) Inventors: Ignacio Lizasoain Hernandez, Madrid (ES); Victor Manuel Gonzalez Muñoz, Becerril de la Sierra-Madrid (ES); Geronimo Fernandez Gomez-Chacon, Madrid (ES); Maria Angeles Moro Sanchez, Colmenar Viejo-Madrid (ES); Maria Elena Martin Palma, Madrid (ES); Ana Moraga Yebenes, Tomelloso-Ciudad Real (ES)

(73) Assignee: APTATARGETS, S.L., Madrid (ES)

( * ) Notice: Subject to any disclaimer, the term of this patent is extended or adjusted under 35 U.S.C. 154(b) by 0 days.

This patent is subject to a terminal disclaimer.

(21) Appl. No.: 16/220,726

(22) Filed: Dec. 14, 2018

(65) Prior Publication Data

US 2019/0211334 A1 Jul. 11, 2019

Related U.S. Application Data

(63) Continuation of application No. 15/322,021, filed as application No. PCT/EP2015/064277 on Jun. 24, 2015, now Pat. No. 10,196,642.

(30) Foreign Application Priority Data

Jun. 24, 2014 (ES) .................................. 201430955

(51) Int. Cl.
| | | |
|---|---|---|
| *C12N 15/115* | (2010.01) | |
| *A61K 31/7088* | (2006.01) | |
| *G01N 33/566* | (2006.01) | |

(52) U.S. Cl.
CPC ........ *C12N 15/115* (2013.01); *A61K 31/7088* (2013.01); *G01N 33/566* (2013.01); *C12N 2310/16* (2013.01); *C12N 2310/53* (2013.01); *G01N 2333/70596* (2013.01)

(58) Field of Classification Search
CPC .......................... C12N 15/115; A61K 31/7088
See application file for complete search history.

(56) References Cited

U.S. PATENT DOCUMENTS

| | | | |
|---|---|---|---|
| 4,522,811 A | 6/1985 | Eppstein et al. | |
| 5,194,599 A | 3/1993 | Froehler et al. | |
| 5,264,562 A | 11/1993 | Matteucci et al. | |
| 5,596,086 A | 1/1997 | Matteucci et al. | |
| 10,196,642 B2 * | 2/2019 | Lizasoain Hernandez ................. | C12N 15/115 |
| 2009/0317802 A1 * | 12/2009 | Bhatia ................ | A61K 49/0002 435/6.11 |
| 2014/0005253 A1 * | 1/2014 | Gelman .............. | C12N 15/1138 514/44 A |

FOREIGN PATENT DOCUMENTS

| | | |
|---|---|---|
| CN | 101365802 A | 2/2009 |
| RU | 2316599 C2 | 1/2005 |
| WO | WO 2006/138681 A3 | 12/2006 |
| WO | WO 2008/076804 A2 | 6/2008 |
| WO | WO 2010/053975 A1 | 5/2010 |
| WO | WO 2010/060030 A1 | 5/2010 |
| WO | WO 2012118911 A1 | 9/2012 |

OTHER PUBLICATIONS

Gooshe et al. Rev. Neurosci 25:713-739 (Year: 2014).*
De Paola et al. Mol Med 18 971-981 (Year: 2012).*
Gambuzza et al. Journal of Neuroimmunology 239; 1-12 (Year: 2011).*
Altschul et al., "Local Alignment Statistics," Methods in Enzymology, 266:460-80, Elsevier, Netherlands (1996).
Altschul et al., "Gapped BLAST and PSI-BLAST: a new generation of protein database search programs," Nucleic Acids Res. 25(17):3389-402, Oxford University Press, England (1997).
Caso, J.R., et al., "Toll-Like Receptor 4 is Involved in Brain Damage and Inflammation after Experimental Stroke," *Circulation* 115:1599-608, American Heart Association, United States (2007).
Chang YC. et al., "Identification And Characterization Of Oligonucleotides That Inhibit Toll-Like Receptor 2-Associated Immune Responses," FASEB Journal 23(9): 3078-3088, Federation of American Societies for Experimental Biology, United States 2009.
Girón et al., "Suppression of inflammatory responses by labdane-type diterpenoids," Toxicol Appl Pharmacol 228:179-89, Elsevier, Netherlands 2008.
Goujon, M., et al., "A new bioinformatics analysis tools framework at EMBL-EBI," *Nucleic Acids Res* 38:W695-9, Oxford Press Company, England (2010).
Hedayat et al., "Prophylactic and Therapeutic Implications of Toll-Like Receptor Ligands," Medicinal Research Reviews 32:294-325, Wiley Interscience, United States 2010.
Karlin et al., "Applications and statistics for multiple high-scoring segments in molecular sequences," Proc. Natl. Acad. Sci., 87:2264-8, National Academy of Science, United States (1990).
Karlin et al., "Methods for assessing the statistical significance of molecular sequence features by using general scoring schemes," Proc. Natl. Acad. Sci., 90:5873-7, National Academy of Science, United States (1993).
Kikin, O., et al., "QGRS Mapper: a web-based server for predicting G-quadruplexes in nucleotide sequences," *Nucleic Acids Res* 34:W676-W682, Oxford Press Company, England (2006).
Martín, M.E., et al., "DNA aptamers selectively target Leishmania infantum H2A protein" *PLoS ONE* 8:e78886, Public Library of Science, United States (2013).

(Continued)

*Primary Examiner* — Brian Whiteman

(74) *Attorney, Agent, or Firm* — Sterne, Kessler, Goldstein & Fox P.L.L.C.

(57) ABSTRACT

The invention relates to a nucleic acid aptamer with the capability of binding specifically to a and inhibiting TLR-4, to a complex comprising said aptamer and a functional group, as well as to pharmaceutical compositions thereof. The invention also relates to uses and methods for detecting TLR-4 and to uses and methods for inhibiting TLR-4. Finally, the invention also relates to an aptamer for use in manufacturing a drug for the treatment of a pathology characterized by an increase in expression of TLR4 and/or an increase in activation of TLR-4.

30 Claims, 12 Drawing Sheets

Specification includes a Sequence Listing.

(56) References Cited

OTHER PUBLICATIONS

Mona, H., et al., "Prophylactic and therapeutic implications of toll-like receptor ligands," *Medicinal Research Reviews* 32:294-325, Wiley Periodicals, United States (2012).
Myers EW and Miller W, "Optimal alignments in linear space," Comput Appl Biosci, 4:11-7, MDPI AG, Switzerland (1988).
Needleman S.B. and Wunsch, C.D., "A General Method Applicable to the Search for Similarities in the Amino Acid Sequence of Two Proteins," Journal of Molecular Biology 48:443-453, Elsevier, Netherlands (1970).
Roger, T., et al., "Protection from lethal gram-negative bacterial sepsis by targeting Toll-like receptor 4," *Proc Natl Acad Sci* 106:2348-52, PNAS, United States (2009).
Schong, K., et al., "Chemical etiology of nucleic acid structure: the alpha-threofuranosyl-(3'-->2') oligonucleotide system," *Science 290*: 1347-1351, American Association for the Advancement of Science, United States (2000).
Watanabe, T et al., "Isolation And Characterization Of RNA Aptamers Specific For The Human Toll-Like Receptor 3 Ectodomain,". Viva Origino. 37:10-18, SSOEL, Japan (2009).
Wittebole, X., et al., "Toll-like Receptor 4 Modulation as a Strategy to Treat Sepsis," *Mediators of Inflammation 2010*:1-9, Hindawi Publishing Corporation, Egypt (2010).
Zuker M., "Mfold web server for nucleic acid folding and hybridization prediction" *Nucleic Acids Res 31*:3406-15, Oxford Press University, England (2003).

\* cited by examiner

APTAMERS SPECIFIC FOR TLR-4 AND USES THEREOF

REFERENCE TO SEQUENCE LISTING SUBMITTED ELECTRONICALLY VIA EFS-WEB

The content of the electronically submitted sequence listing (Name: 3951.0010002_Sequence_listing_ST25.txt; Size: 2,283 bytes; and Date of Creation: Dec. 13, 2018) filed with the application is incorporated herein by reference in its entirety.

CROSS-REFERENCE TO RELATED APPLICATIONS

This application is a continuation of U.S. application Ser. No. 15/322,021 with a 371(c) date of Dec. 23, 2016, which is the U.S. national phase of International Application No. PCT/EP2015/064277, filed Jun. 24, 2015, which claims the benefit of Spanish Patent Application No. P201430955, filed Jun. 24, 2014, all of which are herein incorporated by reference in their entireties.

FIELD OF THE INVENTION

The present invention provides nucleic acid aptamers with the capability of binding specifically to and inhibiting TLR-4 and uses thereof.

BACKGROUND OF THE INVENTION

It is known today that the Central Nervous System (CNS) responds both to bacterial infections and to brain damage, with a very well organized innate immune reaction. The innate immune system can recognize highly conserved molecular patterns through, inter alia, toll-like receptors (TLR).

TLR4 was the first TLR characterized in mammals. Exogenous ligands have been described for this TLR, such as lipopolysaccharide (LPS) of gram-negative bacteria, lipoteichoic acid (LTA) of gram-positive bacteria, or protein F of syncytial respiratory virus. Furthermore, the most important endogenous ligands are HMBG1, HSP-60 of an endogenous origin or derived from *Chlamydia pneumoniae*, HPS-70, fibronectin, fibrinogen, hyaluronic acid, etc., all derived from tissue damage, cell damage and/or from the host's vessels. TLR4 is involved in a large number of highly prevalent pathologies, such as stroke or cerebrovascular disease, acute myocardial infarction, sepsis, atherosclerosis, multiple sclerosis, rheumatoid arthritis, a retinal degenerative disease, and drug addiction, inter alia.

The involvement of innate immunity and, in particular, of TLRs in multiple pathologies has sparked growing interest in the development of agonists and antagonists of these receptors. Agonists have therefore been developed for the possible treatment of cancer, allergic diseases, infections, and as vaccine coadyuvants. In addition, TLR antagonists are being studied in sepsis, in atherosclerosis, in chronic pain and in colitis; in fact there are several antagonists, eritoran (phase III), ibudilast (Av411; phase II) and NI-0101 antibodies (pre-clinical phase), which are being studied in these pathologies.

Patent document WO 2006/138681 describes a method for inhibiting intrahepatic activated T-cell deletion by means of administering a TLR-4 inhibitor, among which TLR-4-specific aptamers are mentioned.

Roger and others (Roger et al., 2009, Proc Natl Acad Sci USA 106:2348-52) describe antibodies specific for the extracellular domain of TLR4. These antibodies provide protection against lethal sepsis of gram-negative bacteria in mice. The therapeutic usefulness of these anti-TLR4 antibodies is also suggested given that treatment is effective when the antibodies are administered up to 4 h after exposure to an endotoxin and up to 13 h after the onset of infection due to *Escherichia coli*.

Therefore, there is a need in the art for new molecules with the capability of binding specifically to and inhibiting TLR-4 and that are useful as therapeutic agents.

BRIEF DESCRIPTION OF THE INVENTION

In a first aspect, the present invention relates to a nucleic acid aptamer with the capability of binding specifically to and inhibiting TLR-4 and comprising a sequence selected from the group consisting of SEQ ID NO: 1 and SEQ ID NO: 2 or a functionally equivalent variant thereof.

In another aspect, the present invention relates to a complex comprising the aptamer of the invention and a functional group.

In another aspect, the present invention relates to the use of the aptamer of the invention or of the complex of the invention for detecting TLR-4.

In another aspect, the present invention relates to the in vitro use of the aptamer of the invention or of the complex of the invention for inhibiting TLR-4.

In another aspect, the present invention relates to an in vitro method for the detection of TLR-4 in a sample comprising
   i) contacting said sample with an aptamer according to the invention, or a complex according to the invention,
   ii) separating the aptamer or complex not bound to TLR-4, and
   iii) detecting the presence of the aptamer or complex bound to the TLR-4 present in the sample.

In another aspect, the present invention relates to an in vitro method for inhibiting TLR-4 in a sample, which comprises contacting a sample comprising TLR-4 with an aptamer according to the invention, or a complex according to the invention, in conditions suitable for inhibiting TLR-4.

In another aspect, the present invention relates to an aptamer of the invention for use in the treatment of a pathology characterized by an increase in expression of TLR4 and/or an increase in activation of TLR-4.

In another aspect, the present invention relates to a pharmaceutical composition comprising at least one aptamer according to the invention or at least one complex according to the invention, optionally in combination with one or more pharmaceutically acceptable carriers, excipients or solvents.

DETAILED DESCRIPTION OF THE INVENTION

Figure 1:
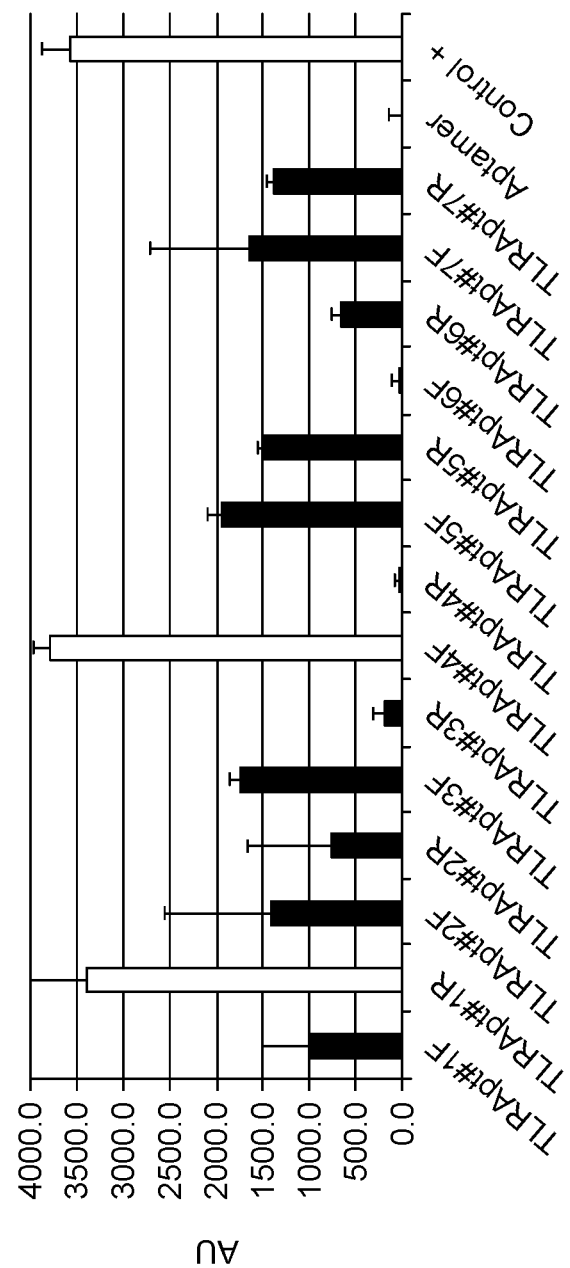
FIG. 1. Recognition of the TLR-4 protein by the aptamers selected by means of ELONA. The human recombinant TLR-4 protein (6×HIS-TLR-4) was cultured at a concentration of 100 ng/well in 96-well microtiter plates and incubated at 4° C. for 16 h. Subsequently, 20 pmol of each of the aptamers labeled with digoxigenin were added to each well and the plate was incubated for 1 h at 37° C. Finally, the plate was incubated with peroxidase-conjugated anti-digoxigenin antibodies and developed using ABTS. An anti-Li H2A DNA aptamer was used as a positive control (Martin et al., 2013, PLoS ONE 8: e78886). All the experiments were performed in triplicate.

The authors of the present invention have selected and characterized two molecules which, due to their sequences, can be three-dimensionally structured in certain pH, temperature and saline concentration conditions, giving them the capability to recognize specifically the TLR-4 protein and modulate its activity. These molecules can inhibit cellular response mediated by receptor TLR-4 in vivo and can reduce the size of brain infarction in animal models of ischemic stroke, giving them a potential therapeutic role.

Aptamer Specific for TLR-4

In a first aspect, the present invention relates to a nucleic acid aptamer with the capability of binding specifically to and inhibiting TLR-4, hereinafter referred to as the "aptamer of the invention", and comprising a sequence selected from the group consisting of SEQ ID NO: 1 (CCGGCACGGGA-CAAGGCGCGGGACGGCGTAGATCAGGTCGACACC) and SEQ ID NO: 2 (GGTGTGCCAATAAACCATATCGC-CGCGTTAGCATGTACTCGGT TGGCCCTAAATAC-GAG), or a functionally equivalent variant thereof.

The term "aptamer", in the context of the present invention, refers to single-stranded nucleic acid chains adopting a specific tertiary structure that allows them to bind to molecular targets with high specificity and affinity, comparable to that of monoclonal antibodies, through interactions other than conventional Watson-Crick base pairing.

The term "nucleic acid", in the context of the present invention, refers to any type of nucleic acid, such as DNA and RNA, and to variants thereof, such as peptide nucleic acid (PNA), locked nucleic acid (LNA), as well as combinations thereof, modifications thereof, including modified nucleotides, etc. The terms "nucleic acid" and "oligonucleotide" and "polynucleotide" are used interchangeably in the context of the present invention. Nucleic acids can be purified from natural sources, produced using recombinant expression systems and, optionally, purified, chemically synthesized, etc. When appropriate, for example, in the case of chemically synthesized molecules, the nucleic acids can comprise nucleoside analogues such as analogues having chemically modified bases or sugars, modifications of the backbone, etc. A nucleic acid sequence is represented in 5'-3' direction unless indicated otherwise.

The term "TLR-4", in the context of the present invention, refers to membrane receptor toll-like receptor 4. Receptor TLR-4 can also be referred to as ARMD10, CD284, TLR4 or hTOLL. In humans, receptor TLR-4 was registered in GenBank under accession number O00206.2 on 27 May 2014, and it is encoded by the TLR4 gene. It is made up of 839 amino acids, of which residues 1-23 constitute the signal sequence, residues 24-631 constitute the extracellular domain, residues 632-652 constitute the transmembrane domain, and residues 653-839 constitute the cytoplasmic domain.

In a particular embodiment, the aptamer can bind specifically to the extracellular domain of TLR-4 (amino acids 24-631).

The present invention contemplates an aptamer comprising a sequence selected from the group consisting of SEQ ID NO: 1 (CCGGCACGGGACAAGGCGCGGGACGGCG-TAGATCAGGTCGACACC) and SEQ ID NO: 2 (GGTGT-GCCAATAAACCATATCGCCGCGTTAGCATG-TACTCGGT TGGCCCTAAATACGAG) or a functionally equivalent variant thereof.

The present invention also contemplates aptamers of the invention that are made up of nucleic acids such as DNA and RNA, as well as of nucleic acid variants and analogues and combinations thereof, modifications thereof, including, without limitation, modified nucleic acid backbones, substitution bonds, modified nucleotides, and ribose or deoxyribose analogues, modified nucleotides, etc., with a capability of binding specifically to and inhibiting TLR-4 of at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 100% of the capability of specifically binding to and inhibiting TLR-4 of the aptamer of sequence SEQ ID NO: 1 or SEQ ID NO: 2. Non-limiting examples of nucleic acid variants and analogues include, without limitation, PNA, LNA and TNA.

The term "nucleic acid variant" or "nucleic acid analogue", in the context of the present invention, refers to nucleic acid variants and analogues including, without limitation, modified nucleic acid backbones, substitution bonds, modified nucleotides, and ribose or deoxyribose analogues. For example, nucleic acid variants according to the present invention can comprise structures with analogue synthetic backbones of the typical phosphodiester backbone. These include, without limitation, phosphorothioate, phosphorodithioate, methylphosphonate, phosphoramidate, alkyl phosphotriester, sulfamate, 3'-thioacetal, methylene(methylimino), 3'-N-carbamate, morpholine carbamate and peptide nucleic acids (PNA), methylphosphonate bonds or alternating methylphosphonate and phosphodiester and benzylphosphonate.

Nucleic acid variants can also contain one or more "substitution" bonds, as is generally understood in the art. Some of these substitution bonds are apolar and contribute to providing the aptamer with a capability of spreading through the membranes. These "substitution" bonds are herein defined as conventional alternative bonds, such as phosphorothioate or phosphoramidate, and are synthesized as described in the commonly available literature. Alternative binding groups include, in a non-limiting manner, embodiments in which a moiety of formula P(O)S, ("thioate"), P(S)S ("dithioate"), P(O)NR'$_2$, P(O)R', P(O)OR$^6$, CO, or CONR'$_2$, wherein R' is H (or a salt) or an alkyl group of 1-12 carbon atoms and R$^6$ is an alkyl group of 1-9 carbon atoms, which binds to adjacent nucleotides through—S— or —O—. Dithioate bonds are described in U.S. patent application Ser. No. 248,517. The present invention also contemplates the use of substitution bonds including internucleotide bonds not based on phosphorus, such as 3'-thioformacetal, (—S—CH$_2$—O—), formacetal (—O—CH$_2$—O—) and 3'-amine internucleotide bonds (—NH—CH$_2$—CH$_2$—) described in U.S. patent application Ser. Nos. 690,786 and 763,130. One or more substitution bonds can be used in the aptamers of the invention for the purpose of even further facilitating binding to TLR-4 or for increasing the stability of the aptamers against nucleases, as well as for providing permeation capability. Not all the bonds within the same aptamer have to be identical, and the present invention therefore contemplates aptamers with all identical bonds as well as aptamers with a variation in the composition of their bonds.

Likewise, nucleic acid variants according to the present invention can also contain ribose or deoxyribose analogue forms which are well-known in the art, including without limitation sugars substituted at 2', such as 2'-O-methyl-ribose, 2'-fluoro-ribose or 2'-azido-ribose, carbocyclic analogues of sugars, α-anomeric sugars, epimeric sugars such as arabinose, xyloses or lyxoses, pyranose sugars, furanose sugars and sedoheptuloses. The nucleic acids can also contain threose nucleic acid (TNA, also referred to as alpha-threofuranosyl oligonucleotides) (see, for example, Schong et al., Science 2000, Nov. 17, 290 (5495): 1347-1351). In particular, the substitution in the position 2' of the residue of furanose is particularly important with respect to the improvement in nuclease stability.

The term "nucleotide", in the context of the present invention, refers to the monomers making up the nucleic acids. The nucleotides are formed by a pentose, a nitrogenous base and a phosphate group, and are bound by means of phosphodiester bonds. The nucleotides that are part of DNA and RNA differ in the pentose, this being deoxyribose and ribose, respectively. The nitrogenous bases, in turn, are divided into purine nitrogenous bases, which are adenine (A) and guanine (G), and into pyrimidine nitrogenous bases, which are thymine (T), cytosine (C) and uracil (U). Thymine only appears in DNA, whereas uracil only appears in RNA. The present invention contemplates the use of modified nucleotides in the aptamer of the invention. The term "modified nucleotide", in the context of the present invention, refers to known natural nucleotides analogues, with similar or improved binding properties. Analogue forms of purines and pyrimidines are well-known in the art and include, without limitation, aziridinylcytosine, 4-acetylcytosine, 5-fluorouracil, 5-bromouracil, 5-carboxymethylaminomethyl-2-thiouracil, 5-carboxymethylaminomethyluracil, inosine, N$_6$-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N$_6$-methyladenine, 7-methylguanine, 5-methylaminomethyluracil, 5-methoxyaminomethyl-2-thiouracil, beta-D-mannosylkeosine, 5-methoxyuracil, 2-methylthio-N-6-isopentenyladenine, uracil-5-oxyacetic acid methyl ester, pseudouracil, keosine, 2-thiocytosine, 5-methyl-2-thiouracil, 2-thiouracil, 4-thiouracil, 5-methyluracil, uracil-5-oxyacetic acid, and 2,6-diaminopurine. In addition to the preceding modified nucleotides, nucleotide residues lacking a purine or a pyrimidine also can be included in the present invention.

In addition to the preceding variants, the nucleic acid variants comprised in the invention also include PNA, LNA and 5'-5' or 3'-3' chains. The term "peptide nucleic acid" or "PNA", in the context of the present invention, refers to an oligonucleotide the backbone of which is made up of repetitive units of N-(2-aminoethyl)-glycine bound by peptide bonds, wherein the different nitrogenous bases are bound to the main chain by a methylene bond (—$CH_2$—) and a carbonyl group (—(C═O)—). The term "locked nucleic acid" or "LNA", in the context of the present invention, refers to a modified RNA nucleotide the ribose moiety of which is modified with an additional bond connecting the oxygen at 2' with the carbon at 4', locking the ribose in the 3'-endo conformation. The term "5'-5' chain" or "3'-3' chain", in the context of the present invention, refers to oligonucleotides in which the nucleotide of the 3' or 5' ends, respectively, is inverted.

As it is used herein, the term "functionally equivalent variant" refers to aptamers with sequences substantially similar to SEQ ID NO: 1 or SEQ ID NO: 2 maintaining the capability of specifically binding to and inhibiting TLR-4. A functionally equivalent variant of the aptamer of the invention can be a nucleic acid sequence derived from SEQ ID NO: 1 or SEQ ID NO: 2 comprising the addition, substitution or modification of one or more nucleotides. By way of illustration, functionally equivalent variants of the aptamer of the invention include sequences comprising the addition of 1 nucleotide, 2 nucleotides, 3 nucleotides, 4 nucleotides, 5 nucleotides, 10 nucleotides, 15 nucleotides, 20 nucleotides, 25 nucleotides, 30 nucleotides, 35 nucleotides, 40 nucleotides, 45 nucleotides, 50 nucleotides, 60 nucleotides, 70 nucleotides, 80 nucleotides, 90 nucleotides, 100 nucleotides, 150 nucleotides, 200 nucleotides, at least 500 nucleotides, at least 1000 nucleotides or more at the 5' end of the sequence SEQ ID NO: 1 or SEQ ID NO: 2, and/or comprising the addition of 1 nucleotide, 2 nucleotides, 3 nucleotides, 4 nucleotides, 5 nucleotides, 10 nucleotides, 15 nucleotides, 20 nucleotides, 25 nucleotides, 30 nucleotides, 35 nucleotides, 40 nucleotides, 45 nucleotides, 50 nucleotides, 60 nucleotides, 70 nucleotides, 80 nucleotides, 90 nucleotides, 100 nucleotides, 150 nucleotides, 200 nucleotides, at least 500 nucleotides, at least 1000 nucleotides or more at the 3' end of the sequence SEQ ID NO: 1 or SEQ ID NO: 2, and maintaining a capability of specifically binding to and inhibiting TLR-4 of at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 100% of the capability of specifically binding to and inhibiting TLR-4.

The present invention also includes aptamers comprising nucleotide sequences with a sequence identity of at least 70%, at least 75%, at least 80%, at least 85%, at least 90%, at least 91%, at least 92%, at least 93%, at least 94%, at least 95%, at least 96%, at least 97%, at least 98%, or at least 99% with the sequences SEQ ID NO: 1 or SEQ ID NO: 2 and maintaining a capability of specifically binding to and inhibiting TLR-4 of at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 100% of the capability of specifically binding to and inhibiting TLR-4.

The terms "identity", "identical" or "percent identity" in the context of two or more nucleic acids, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences. One such non-limiting example of a sequence alignment algorithm is the algorithm described in Karlin et al., 1990, Proc. Natl. Acad. Sci., 87:2264-8, as modified in Karlin et al., 1993, Proc. Natl. Acad. Sci., 90:5873-7, and incorporated into the NBLAST and XBLAST programs (Altschul et al., 1991, Nucleic Acids Res., 25:3389-402). In certain embodiments, Gapped BLAST can be used as described in Altschul et al., 1997, Nucleic Acids Res. 25:3389-402. BLAST-2, WU-BLAST-2 (Altschul et al., 1996, Methods in Enzymology, 266:460-80), ALIGN, ALIGN-2 (Genentech, South San Francisco, Calif.) or Megalign (DNASTAR) are additional publicly available software programs that can be used to align sequences. In certain embodiments, the percent identity between two nucleotide sequences is determined using the GAP program in GCG software (e.g., using a NWSgapdna.CMP matrix and a gap weight of 40, 50, 60, 70, or 90 and a length weight of 1, 2, 3, 4, 5, or 6). In certain alternative embodiments, the GAP program in the GCG software package, which incorporates the algorithm of Needleman and Wunsch (J. Mol. Biol. 48:444-53 (1970)) can be used to determine the percent identity between two amino acid sequences (e.g., using either a Blossum 62 matrix or a PAM250 matrix, and a gap weight of 16, 14, 12, 10, 8, 6, or 4 and a length weight of 1, 2, 3, 4, 5). Alternatively, in certain embodiments, the percent identity between nucleotide or amino acid sequences is determined using the algorithm of Myers and Miller (CABIOS, 4:11-7 (1989)). For example, the percent identity can be determined using the ALIGN program (version 2.0) and using a PAM120 with residue table, a gap length penalty of 12 and a gap penalty of 4. Appropriate parameters for maximal alignment by particular alignment software can be determined by one skilled in the art. In certain embodiments, the default parameters of the alignment software are used. In certain embodiments, the percentage identity "X" of a first amino acid sequence to a second sequence amino acid is calculated as 100×(Y/Z), where Y is the number of amino acid residues scored as identical matches in the alignment of the first and second sequences (as aligned by visual inspection or a particular sequence alignment program) and Z is the total number of residues in the second sequence. If the second sequence is longer than the first sequence, then the percent identity may be determined only in the region of overlap between said first and second sequences. In this case, the same formula as above can be used but using as Z value the length of the region wherein the first and second sequence overlaps, said region having a length which is substantially the same as the length of the first sequence.

As a non-limiting example, whether any particular polynucleotide has a certain percentage sequence identity (e.g., is at least 80% identical, at least 85% identical, at least 90% identical, and in some embodiments, at least 95%, 96%, 97%, 98%, or 99% identical) to a reference sequence can, in certain embodiments, be determined using the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, Advances in Applied Mathematics 2:482-9 (1981), to find the best segment of homology between two sequences. When using Bestfit or any other sequence alignment program to determine whether a particular sequence is, for instance, 95% identical to a reference sequence according to the present invention, the parameters are set such that the percentage of identity is calculated over the full length of the reference nucleotide sequence and that gaps in homology of up to 5% of the total number of nucleotides in the reference sequence are allowed.

In some embodiments, two nucleic acids of the invention are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. Identity can exist over a region of the sequences that is at least about 10, about 20, about 40-60 residues in length or any integral value therebetween, and can be over a longer region than 60-80 residues, for example, at least about 90-100 residues, and in some embodiments, the sequences are substantially identical over the full length of the sequences being compared, such as the coding region of a nucleotide sequence for example.

The term "specific binding" or "specific binding to TLR-4", in the context of the present invention, refers to the non-covalent physical association between two molecules, the aptamer of the invention and receptor TLR-4. The binding between the aptamer of the invention and receptor TLR-4 is considered specific if the binding strength between both is at least 10 times, at least 15 times, at least 20 times, at least 25 times, at least 50 times, at least 75 times or at least 100 times greater than the binding strength between the aptamer of the invention and an irrelevant molecule. The binding between the aptamer of the invention and receptor TLR-4 is also considered specific if the equilibrium dissociation constant Kd is $10^{-3}$ M or less, $10^{-4}$ M or less, $10^{-5}$ M or less, $10^{-6}$ M or less, $10^{-7}$ M or less, $10^{-8}$ M or less, $10^{-9}$ M or less, $10^{-10}$ M or less, $10^{11}$ M or less, or $10^{-12}$ M or less under the conditions used, for example, in physiological conditions, cell culture conditions or conditions that allow cell survival.

The capability of the aptamer of the invention of binding specifically to TLR-4 can be determined by means of a range of assays that are available in the art. Preferably, the capability of the aptamer of the invention for the specific binding to TLR-4 is determined by means of in vitro binding assays, such as the enzyme-linked oligonucleotide assay (ELONA), the enzyme-linked aptamer sorbent assay (ELASA), precipitation and quantitative PCR (qPCR), or by fluorescence techniques such as aptahistochemistry, aptacytochemistry, fluorescence microscopy or flow cytometry. Likewise, both the capability of specific binding to TLR-4 and the affinity of the aptamer for TLR-4 can be determined by techniques well-known by the person skilled in the art, such as gel mobility shift assay, surface plasmon resonance (SPR), kinetic capillary electrophoresis and fluorescence binding assay. Briefly, the fluorescence binding assay consists of the incubation of magnetic balls coated with TLR-4 with different concentrations (for example, from 0 to 100 nM) of the aptamer of the invention labeled (for example, with carboxyfluorescein, FAM), and the subsequent elution and detection of the bound aptamers; the dissociation constants (Kd) are calculated by non-linear fit analysis.

The term "inhibition of TLR-4", in the context of the present invention, refers to the blocking or disminution of the activity of TLR-4, i.e., the transduction of the receptor TLR-4-mediated signal. It is considered that the activity of TLR-4 is inhibited by an inhibitory agent or antagonist when its activity is at least 95%, at least 90%, at least 85%, at least 80%, at least 75%, at least 70%, at least 65%, at least 60%, at least 55%, at least 50%, at least 45%, at least 40%, at least 35%, at least 30%, at least 25%, at least 20%, at least 15%, at least 10%, at least 5%, at least 1%, or less of the activity of TLR-4 in the presence of its natural agonist LPS.

The capability of the aptamer of the invention of inhibiting TLR-4 can be determined by means of a range of assays that are available in the art. Preferably, the capability of inhibiting TLR-4 of the aptamer of the invention is determined by means of in vitro assays with cells expressing recombinant TLR-4 and a reporter gene, the expression of which is associated with the activation of recombinant TLR-4. The person skilled in the art will recognize that there are multiple variants of this method, depending on the cell and the recombinant gene used. An example of this assay is included in the examples of the present invention (section on "Materials and methods" and Example 2). Other available techniques include the determination of the levels of inflammatory cytokines, such as IL-1, IL-8, TNF-alpha and IL-12, released by cells that express TLR-4.

In a particular embodiment, the aptamer of the invention consists of between 30 and 200 nucleotides, preferably between 35 and 150 nucleotides, more preferably between 40 and 100 nucleotides, even more preferably between 45 and 80 nucleotides.

In another particular embodiment, the aptamer of the invention comprises a sequence selected from the group consisting of SEQ ID NO: 3 (GTTGCTCGTATTTAGGGC-CACCGGCACGGGACAAGGCGCGGGACGGCGTAG ATCAGGTCGACACCAGTCTTCATCCGC) and SEQ ID NO: 4 (GCGGATGAAGAC TGGTGTGCCAATAAAC-CATATCGCCGCGTTAGCATGTACTCGGTTGGC-CCTAAAT ACGAGCAAC). The sequence SEQ ID NO: 3 is a functionally equivalent variant of SEQ ID NO: 1 and the sequence SEQ ID NO: 4 is a functionally equivalent variant of SEQ ID NO: 2.

In a particular embodiment, the nucleic acid is DNA. In another particular embodiment, the nucleic acid is RNA. In another particular embodiment, the nucleic acid is PNA. In another particular embodiment, the nucleic acid is LNA. In another particular embodiment, the nucleic acid is TNA.

In another particular embodiment, the TLR-4 is a TLR-4 selected from the group formed by mouse, rat, rabbit, pig, cat, dog, horse, primate, and human TLR-4. In a preferred embodiment, the TLR-4 is a human TLR-4.

The production of the aptamer of the invention can be carried out following conventional methods in the art. Non-limiting examples of techniques for the production of aptamers include enzymatic techniques, such as transcription, recombinant expression systems and standard solid phase (or solution phase) chemical synthesis, all commercially available. When appropriate, for example, in the event that the aptamer of the invention comprises nucleic acid variants such as those described above, nucleotide analogues such as analogues having chemically modified bases or sugars, backbone modifications, etc., the aptamer of the invention will be produced by means of chemical synthesis. Alternatively, expression will be the technique preferred for the production of aptamers when said aptamers have a length of 200 nucleotides or more. The aptamers produced by or any of the preceding techniques can optionally be purified by methods that are well known in the art.

Complex of the Invention

As the person skilled in the art will appreciate, the features of the small size, stability and easy production of the aptamer of the invention enable said aptamer to be presented bound to a second molecule. That is particularly advantageous when the second molecule is a functional group. The result of the binding of the aptamer of the invention and a functional group is a complex presenting the combination of functions of both, i.e., a complex with the capability of specifically binding to and inhibiting TLR-4 and with the activity associated with the functional group.

Therefore, in another aspect, the present invention refers to a complex, hereinafter referred to as the "complex of the invention", comprising a nucleic acid aptamer with the capability of binding specifically to and inhibiting TLR-4, comprising a sequence selected from the group consisting of SEQ ID NO: 1 and SEQ ID NO: 2 or a functionally equivalent variant thereof and a functional group.

The term "aptamer" has been described in detail in relation to the Definitions and the Aptamer specific for TLR-4 (supra) and its definitions and particularities apply likewise in the context of the complex of the invention.

The term "functional group", in the context of the present invention, refers to compounds suitable for performing at least one function. Said function includes, without limitation, the capability of binding specifically to TLR-4 or to other receptors TLR, the capability of inhibiting TLR-4 or other receptors TLR, the capability of being both directly and indirectly detectable, the capability of inducing cell death, the capability of carrying a therapeutic payload, etc. As the person skilled in the art will understand, a functional group can have associated therewith one or multiple functions. Non-limiting examples of functional groups include detectable reagents and drugs. These functional groups act like imaging agents, drugs, etc.

Therefore, in a particular embodiment, the functional group is selected from a detectable reagent, a drug and a nanoparticle.

In another particular embodiment, the functional group is a detectable reagent. The terms "detectable reagent", "imaging agent" and "contrast agent" are used herein interchangeably and refer to a biocompatible compound, the use of which facilitates the differentiation of different parts of the image, by increasing the "contrast" between those different regions of the image. The term "contrast agents" thus encompasses agents that are used to enhance the quality of an image that may nonetheless be generated in the absence of such an agent (as is the case, for instance, in MRI), as well as agents that are prerequisites for the generation of an image (as is the case, for instance, in nuclear imaging). Suitable contrast agent include, without limitation, contrast agents for radionuclide imaging, for computerized tomography (CT), for Raman spectroscopy, for Magnetic resonance imaging (MRI) and for optical imaging.

Detectable reagents for radionuclide imaging include radiopharmaceuticals are commonly labeled with positron-emitters such as $^{11}$C, $^{13}$N, $^{15}$O, $^{18}$F, $^{82}$Rb, $^{62}$Cu, $^{64}$Cu, and $^{68}$Ga $^{86}$Y, $^{124}$I, $^{213}$Bi and $^{211}$At. SPECT radiopharmaceuticals are commonly labelled with positron emitters such as $^{94}$mTc, $^{201}$Tl and $^{67}$Ga. Radionuclide imaging modalities (positron emission tomography, (PET); single photon emission computed tomography (SPECT)) are diagnostic cross-sectional imaging techniques that map the location and concentration of radionuclide-labeled radiotracers. PET and SPECT can be used to localize and characterize a radionuclide by measuring metabolic activity. PET and SPECT provide information pertaining to information at the cellular level, such as cellular viability. In PET, a positron emitter is administered to the patient, which can be monitored as the substance moves through the body. In certain embodiments of the invention, a complex according to the invention is used for PET or SPECT imaging in vivo. Closely related to PET is single-photon emission computed tomography, or SPECT. The major difference between the two is that instead of a positron-emitting substance, SPECT uses a radioactive tracer that emits low-energy photons. Other non-limiting examples of radionuclides include gamma emission isotopes, such as $^{99m}$Tc, $^{123}$I and $^{111}$In, which can be used in radioscintigraphy using gamma cameras or computerized single photon emission tomography, as well as beta emitters, such as $^{131}$I $^{90}$Y, $^{99m}$Tc, $^{177}$Lu and $^{67}$Cu". The person skilled in the art will understand that the radionuclides may also be used for therapeutic purposes.

Detectable reagents for CT imaging include, for example, iodinated or brominated contrast media. Examples of these agents include iothalamate, iohexyl, diatrizoate, iopamidol, ethiodol and iopanoate. Gadolinium agents have also been reported to be of use as a CT contrast agent. For example, gadopentate agents have been used as a CT contrast agent. Computerized tomography (CT) is contemplated as an imaging modality in the context of the present invention. By taking a series of X-rays, sometimes more than a thousand, from various angles and then combining them with a computer, CT made it possible to build up a three-dimensional image of any part of the body. A computer is programmed to display two-dimensional slices from any angle and at any depth. In CT, intravenous injection of a radiopaque contrast agent such as those described herein can assist in the identification and delineation of soft tissue masses when initial CT scans are not diagnostic.

Detectable reagents for optical imaging include, for example, fluorescein, a fluorescein derivative, indocyanine green, Oregon green, a derivative of Oregon green derivative, rhodamine green, a derivative of rhodamine green, an eosin, an erythrosin, Texas red, a derivative of Texas red, malachite green, nanogold sulfosuccinimidyl ester, cascade blue, a coumarin derivative, a naphthalene, a pyridyloxazole derivative, cascade yellow dye, dapoxyl dye, and various other fluorescent compounds, such as Cy3, Cy2, Cy5, the Alexa Fluor® fluorescent label family (Molecular Probes, Inc.), carboxyfluorescein (FAM) and fluorescein isothiocyanate (FITC).

In another preferred embodiment, the detectable reagent is a protein. The term "protein", in the context of the present invention, refers to macromolecules consisting of one or more amino acid chains. The proteins are responsible for carrying out a diverse group of cell functions based on their ability to specifically bind other molecules. The proteins can be bound to other proteins as well as to small substrate molecules. Non-limiting examples of proteins suitable for the purposes of the present invention include, without limitation, enzymes, fluorescent proteins, luminescent proteins and antigens.

In an even more preferred embodiment, the protein is an enzyme. The term "enzyme", in the context of the present invention, refers to a protein working as a highly selective catalyst, accelerating both the speed and the specificity of the metabolic reaction for which it is specific. Non-limiting examples of enzymes suitable for the invention include, without limitation, horseradish peroxidase (HRP) and alkaline phosphatase. As the person skilled in the art will understand, the enzymes suitable for use in the present invention are indirectly detectable as a result of their capability of catalyzing modifying a substrate in a compound detectable by colorimetry, chemiluminescence or fluorimetry. Examples of suitable substrates include, without limitation, p-Nitrophenyl phosphate (PNPP), 2,2'-azinobis[3-ethylbenzothiazolin-6-sulfonic acid] (ABTS), o-phenylenediamine (OPD), and 3,3',5,5'-tetramethylbenzidine (TMB).

Bioluminescent proteins or photoproteins are a particular case of oxidative enzymes capable of carrying out a chemical reaction of their specific prosthetic groups, resulting in light emission without requiring prior excitation. Non-limiting examples of bioluminescent proteins include firefly luciferase, *Renilla* luciferase and aequorin.

In another even more preferred embodiment, the protein is a fluorescent protein. The term "fluorescent protein", in the context of the present invention, refers to a protein with the capability of emitting light when it is excited at a wavelength suitable for excitation. Non-limiting examples of fluorescent proteins that can be used in the complex of the invention include, without limitation, GFP, GFPuv, BFP, CFP, YFP, EBFP2, mCerulean, mCerulean3, mVenus, mTurquoise, T-Sapphire, citrine, amFP486, zFP506, zFP538, drFP, DsRed, mCherry, dTomate, mTFP1, TagRFP-T, mKO2, mRuby, mKate, mAmetrine, REACh, R-phycoerythrin (R-PE) and Allophycocyanin (APC).

In another even more preferred embodiment, the protein is a luminescent protein. The term "luminescent protein", in the context of the present invention, refers to a protein capable of emitting light when it is excited at a wavelength suitable for excitation. Non-limiting examples of fluorescent proteins that can be used in the complex of the invention include, without limitation, the proteins included in Table 1, together with their corresponding excitation and emission wavelengths.

In another even more preferred embodiment, the protein is an antigen. The term "antigen", in the context of the present invention, refers to a molecule that induces an immune response in the body. Therefore, an antigen can be used for generating an antibody that recognizes it and binds specifically to it. Non-limiting examples of antigens include, inter alia, tumor antigens, such as the carcinoembryonic antigen (CEA), HER2, prostate specific antigen (PSA) and tissue plasminogen activator and its recombinant variants, such as Activase®, as well as bacterial antigens, allergens, etc. As the person skilled in the art will understand, the antigens suitable for use in the present invention are indirectly detectable as a result of their capability of being specifically recognized by an antibody.

In another preferred embodiment, the detectable reagent is a haptene. The term "haptene", in the context of the present invention, refers to a group of chemical compounds having a small molecular size (<10,000 Da) which are antigenic but unable to induce by themselves an specific immune reaction. The chemical coupling of a haptene to a large immunogenic protein, called carrier, generates an haptene-immunogenic carrier conjugate which is able to induce a specific immune reaction. Non-limiting examples of vitamins include biotin (vitamin B7), digoxigenin, dinitrophenol (DNP) and nitro-iodophenol (NIP). In a more preferred embodiment, the vitamin is biotin. The term "biotin", in the context of the present invention, refers to a water- and alcohol-soluble heat-stable vitamin, also referred to as vitamin H and vitamin B7, characterized by specifically binding to avidin with the highest affinity described to date of $Kd=10^{-15}$ M. As the person skilled in the art will understand, biotin is indirectly detectable as a result of its capability of being specifically recognized by avidin or variants thereof, such as streptavidin and neutravidin.

In another particular embodiment, the functional group is a drug. The term "drug", in the context of the present invention, refers to a chemical substance used in the treatment, cure or prevention of a disease or condition, such as a pathology characterized by an increase in expression of TLR-4 and/or an increase in activation of TLR-4. The term "pathology characterized by an increase in expression of TLR-4 and/or an increase in activation of TLR-4" is described in detail in the context of the medical uses of the invention and its definition and particularities are herein included by reference.

The person skilled in the art will immediately know which agents are indicated for the treatment of a disease in particular. Almost all the agents that are indicated for the treatment of a pathology characterized by an increase in expression of TLR-4 and/or an increase in activation of TLR-4 can be comprised in the complex of the invention, although the TLR-4 antagonist agents and anti-inflammatory agents are particularly preferred. Although numerous types of drugs can be used in the context of the invention, in a preferred embodiment, the present invention contemplates that the drug is selected from the group including, without limitation, TLR-4 antagonists, such as naloxone, naltrexone, LPS, ibudilast, propentofylline, amitriptyline, ketotifen, cyclobenzaprine, mianserin and imipramine; anti-platelet drugs, such as aspirin and clopidogrel; anti-coagulants, such as heparin, acenocumarol, warfarin, dabigatran and rivaroxaban; and antioxidants, such as edaravone. Although it has already been mentioned in the context of detectable reagents, tissue plasminogen activator and its recombinant variants can be likewise considered as a drug due to their thrombolytic action.

The present invention contemplates that the drug is a nucleic acid. Therefore, in a preferred embodiment the drug is a nucleic acid. Nucleic acids suitable as drugs in the context of the complex of the invention include antisense RNA, antisense DNA and small interfering RNA, which have the capability of silencing the expression of genes involved in a pathology characterized by an increase in expression of TLR-4 and/or an increase in activation of TLR-4, including, without limitation, the NFKB1, RIPK3, IFNB1, LY96 (MD-2), IRF3, TLR3, TIRAP (Mal), TICAM1 (TRIF), RIPK1, TRAF6, CD14, TRAM, IKBKG (IKK-gamma), IFNA1 and TLR4 genes. The term "antisense RNA", in the context of the present invention, refers to a single-stranded RNA the nucleotide sequence of which is complementary for a target messenger RNA, thereby interfering with the expression of the respective gene. The term "antisense DNA", in the context of the present invention, refers to a single-stranded DNA the nucleotide sequence of which is complementary for a target messenger RNA, thereby interfering with or silencing the expression of the respective gene. The term "small interfering RNA" or "siRNA", in the context of the present invention, refers to a double-stranded RNA with a length of 20 to 25 nucleotides which is highly specific for the nucleotide sequence of its target messenger RNA, thereby interfering with the expression of the respective gene.

The present invention contemplates that the drug is a peptide. Therefore, in a preferred embodiment the drug is a peptide. The term "peptide", in the context of the present invention, refers to a short chain of amino acids bound by peptide bonds. The peptide will comprise at least 2 amino acids, at least 3 amino acids, at least 4 amino acids, at least 5 amino acids, at least 10 amino acids, at least 15 amino acids, at least 20 amino acids, at least 30 amino acids, at least 40 amino acids, at least 50 amino acids, at least 60 amino acids, or at least 70 amino acids. Suitable for the purposes of this invention are, inter alia, peptides with the capability of binding to a target and of inducing or inhibiting cell signaling. The term "target binding peptide", in the context of the present invention, refers to a peptide comprising a target binding region. The term "signaling peptide", in the context of the present invention, refers to a peptide with the capability of provoking cell signaling, such as cell receptor agonist peptides. The amino acid sequences suitable for target molecule binding include molecular recognition consensus sequences that are well-known in the art.

In another particular embodiment, the functional group is a nanoparticle. The term "nanoparticle", in the context of the present invention, refers to colloidal systems of the spherical type, rod type, polyhedron type, etc., or similar shapes, having a size less than 1 micrometer (μm), which are individually found or are found forming organized structures (dimers, trimers, tetrahedrons, etc.), dispersed in a fluid (aqueous solution). In a particular embodiment, the nanoparticles suitable for putting the invention into practice have a size less than 1 μm, generally comprised between 1 and 999 nanometers (nm), typically between 5 and 500 nm, preferably between about 10 and 150 nm. In a particular embodiment, the nanoparticles of the invention typically have a mean particle diameter ranging from 2 to 50 nm, preferably from 5 to 20 nm, more preferably of 13 nm. The mean particle diameter is the maximum mean particle dimension, with the understanding that the particles are not necessarily spherical. The shape of said nanoparticles can widely vary; advantageously, said nanoparticles will adopt any optically efficient shape such as spheres, rods, stars, cubes, polyhedrons or any other variant as well as complex associations of several particles; in a particular embodiment, the shape of the nanoparticles for putting the invention into practice is spherical or substantially spherical. The shape can be suitably evaluated by conventional light or by means of electron microscopy techniques.

Nanoparticles suitable for use in the present invention include polymeric nanoparticles, lipid nanoparticles and metal nanoparticles.

Polymeric nanoparticles are formed by a polymeric matrix which is attached to the aptamer. Non-limiting examples of biocompatible polymers that may be useful in the polymeric nanoparticules according to the present invention include polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, or polyamines, polyglutamate, dextran, polyanhydrides, polyurethanes, polymethacrylates, polyacrylates or polycyanoacrylates.polydioxanone (PDO), polyhydroxyalkanoate, polyhydroxybutyrate, poly(glycerol sebacate), polyglycolide, polylactide, PLGA, polycaprolactone or combinations thereof.

Alternatively, the nanoparticles of the invention may be lipid nanoparticles such as a liposome or a micelle. Formation of micelles and liposomes from, for example, vesicle-forming lipids, is known in the art. Vesicle-forming lipids refer to lipids that spontaneously form lipid bilayers above their gel-to-liquid crystalline phase transition temperature range. Such lipids typically have certain features that permit spontaneous bilayer formation, such as close to identical cross-section areas of their hydrophobic and hydrophilic portions permitting packing into lamellar phases. Lipids capable of stable incorporation into lipid bilayers, such as cholesterol and its various analogs, can be incorporated into the lipid bilayer during bilayer formation. The vesicle-forming lipids are preferably lipids having two hydrocarbon chains, typically acyl chains, and a head group, either polar or nonpolar. There are a variety of synthetic vesicle-forming lipids and naturally-occurring vesicle-forming lipids, including the phospholipids, such as phosphatidylcholine, phosphatidylethanolamine, phosphatidic acid, phosphatidylinositol, and sphingomyelin, where the two-hydrocarbon chains are typically between about 14-22 carbon atoms in length, and either saturated or having varying degrees of unsaturation. The above-described lipids and phospholipids whose acyl chains have varying degrees of saturation can be obtained commercially or prepared according to published methods. Other suitable lipids include phospholipids, sphingolipids, glycolipids, and sterols, such as cholesterol.

The term "liposome" refers to vesicles comprised of one or more concentrically ordered lipid bilayers, which encapsulate an aqueous phase. The aqueous phase typically contains the compound to be delivered to a target site. Upon reaching a target site, the liposome fuses with the plasma membranes of target cells, i.e. cells expressing TLR-4, thereby releasing the compound into the cytosol. Alternatively, the liposome is endocytosed or otherwise taken in by the target cells as the content of a transport vesicle (e.g., an endosome or phagosome). Once in the transport vesicle, the liposome either degrades or fuses with the membrane of the vesicle and releases its contents. A variety of methods known to the skilled person are available for preparing liposomes, such as sonication, extrusion, high pressure/homogenization, micro fluidization, detergent dialysis, calcium-induced fusion of small liposome vehicles and ether fusion methods, all of which are well known in the art.

Polymeric and lipidic nanoparticles can additionally include a coating of a amphiphilic compound that surrounds the polymeric material forming a shell for the particle or a stealth material that can allow the particles to evade recognition by immune system components and increase particle circulation half-life.

Alternatively, the nanoparticles of the invention may be a metal nanoparticle. The term "metal nanoparticle" refers to a nanoparticle comprising a metal and showing the optical property known as the surface plasmon phenomenon, i.e., a plasmonic metal. This phenomenon consists of the collective vibration of the electrons of the metal surface, producing an absorption band located in the ultraviolet-visible spectrum (typical of the metal and of the size of the nanoparticles) at the wavelength where the resonance condition occurs in said electrons. The surface plasmon of a metal can be determined by means of any spectroscopic technique known in the state of the art, such as surface plasmon resonance (SPR) spectroscopy, whereby the metal atoms are subjected to an electromagnetic beam or surface plasmon resonance fluorescence spectroscopy (SPFS) based on the detection of the variation of the refractive index of the metal atoms when they are subjected to a photon beam. As defined herein, a "plasmonic metal" is a metal characterized by showing the property of optics known as the surface plasmon phenomenon. The variation of the plasmonic response is particularly evident when several nanoparticles are located close to one another, given that this causes the coupling of their respective near fields, generating a new surface plasmon. In a preferred embodiment, said metal is selected from the group consisting of gold, silver, copper, aluminum, platinum, iron, cobalt, palladium and combinations thereof.

A preferred embodiment of metal nanoparticles is a core-shell nanoparticle, which contains a metal core and a porous shell. Examples of core-shell metal nanoparticles include magnetic mesoporous silica nanoparticles, which are well-known in the art. Thus, in a particularly preferred embodiment, the nanoparticle is a magnetic mesoporous silica nanoparticle.

The nanoparticles may be functionalized by adding a coating on its surface. For biological applications, the surface coating should be polar to give high aqueous solubility and prevent nanoparticle aggregation. In serum or on the cell surface, highly charged coatings promote non-specific binding, whereas polyethylene glycol linked to terminal hydroxyl or methoxy groups repel non-specific interactions.

Aptamers can be linked to nanoparticles ideally by a covalent link, preferably on the nanoparticle surface. Preferably, aptamers should be present in a controlled number per nanoparticle.

Binding between an aptamer of the invention and a functional group for generating the complex of the invention can be carried out by means of conjugation techniques that are well-known by the person skilled in the art. The result is a covalent bond between the aptamer of the invention and the functional group. The conjugation can involve binding of primary amines of the 3' or 5' ends of the aptamer of the invention to the functional group during chemical synthesis of the aptamer. Alternatively, conjugation can be done by means of conventional cross-linking reactions, having the advantage of the much greater chemical reactivity of primary alkyl-amine labels with respect to the aryl amines of the nucleotides themselves. Methods of conjugation are well-known in the art and are based on the use of cross-linking reagents. The cross-linking reagents contain at least two reactive groups which target groups such as primary amines, sulfhydryls, aldehydes, carboxyls, hydroxyls, azides and so on and so forth, in the molecule to be conjugated. The cross-linking agents differ in their chemical specificity, spacer arm length, spacer arm composition, cleavage spacer arm, and structure. For example, conjugation of complexes according to the invention can be carried out directly or through a linking moiety, through one or more non-functional groups in the aptamer and/or the functional group, such as amine, carboxyl, phenyl, thiol or hydroxyl groups. More selective bonds can be achieved by means of the use of a heterobifunctional linker. It is possible to use conventional linkers, such as diisocyanates, diisothiocyanates, bis(hydroxysuccinimide) esters, carbodiimides, maleimide-hydroxysuccinimide esters, glutaraldehyde and the like, or hydrazines and hydrazides, such as 4-(4-N-maleimidophenyl) butyric acid hydrazide (MPBH).

Another approach consists of labeling the aptamers during synthesis by means of PCR using primers labeled, for example, with a fluorophore. To that end, there are various commercial establishments available for the person skilled in the art.

Additionally, in the particular embodiment in which the functional group is a radionuclide, binding between an aptamer according to the invention and the radionuclide can be carried out by means of chemical coordination, wherein the atoms of the aptamer involved in the binding donate electrons to the radionuclide. Coordination reactions are well-known in the art and will depend on the radionuclide and the reactive group involved in the aptamer.

In Vitro Uses of the Invention

A. In Vitro Uses for Detecting TLR-4

The present invention also contemplates in vitro uses of a nucleic acid aptamer with the capability of binding specifically to and inhibiting TLR-4 and comprising a sequence selected from the group consisting of SEQ ID NO: 1 and SEQ ID NO: 2 or a functionally equivalent variant thereof, and of a complex comprising a nucleic acid aptamer with the capability of binding specifically to and inhibiting TLR-4 and comprising a sequence selected from the group consisting of SEQ ID NO: 1 and SEQ ID NO: 2 or a functionally equivalent variant thereof and a functional group, for detecting TLR-4.

Therefore, in another aspect, the present invention refers to an in vitro use of a nucleic acid aptamer with the capability of binding specifically to and inhibiting TLR-4 and comprising a sequence selected from the group consisting of SEQ ID NO: 1 and SEQ ID NO: 2 or a functionally equivalent variant thereof for detecting TLR-4.

Therefore, the capability of an aptamer according to the invention of binding specifically to TLR-4 can be exploited for the indirect detection of TLR-4 through the aptamer according to the invention. For this purpose, the person skilled in the art will recognize that subsequent detection of said aptamer is required. Aptamer detection techniques are well-known in the art and include, for example, the use of antibodies or probes specific for the aptamer. Therefore, once the aptamer according to the invention is bound to TLR-4, an antibody or probe specific for the aptamer, which in turn can be labeled with a detectable reagent, or which can be detected indirectly by means of a secondary antibody or probe, would be applied. The technique used for detecting TLR-4 will then depend on the type of detectable reagent, being able to be techniques based, for example, on fluorimetry, colorimetry or radioactivity.

The term "probe" or "hybridization probe", in the context of the present invention, refers to a variable-length DNA or RNA fragment, generally between 10 and 1000 bases in length, which is used for detecting the presence of single-stranded nucleic acids (DNA or RNA) which are complementary to the sequence in the probe. The probe is hybridized to the target single-stranded nucleic acid, the base sequence of which allows base pairing due to complementarity between the probe and the target nucleic acid. For detecting hybridization of the probe to its target sequence, the probe is labeled with a detectable reagent, such as a radionuclide, a fluorophore or digoxigenin, inter alia.

The detection of TLR-4 with the aptamer of the invention can be carried out by means of in vitro binding assays, such as the enzyme-linked oligonucleotide assay (ELONA), the enzyme-linked aptamer sorbent assay (ELASA), precipitation and quantitative PCR (qPCR), gel mobility shift assay, Western Blotting, surface plasmon resonance (SPR), kinetic capillary electrophoresis, the fluorescence binding assay, aptahistochemistry, aptacytochemistry, fluorescence microscopy or flow cytometry.

In another particular embodiment of the in vitro uses of the invention, the detection of TLR-4 is performed by means of a method selected from the group consisting of ELONA, aptacytochemistry, aptahistochemistry and flow cytometry.

The term "ELONA" or "enzyme-linked oligonucleotide assay", in the context of the present invention, refers to a technique analogous to enzyme-linked immunosorbent assay (ELISA), wherein the antibody that is used for detecting the molecule of interest, in this case TLR-4, is exchanged for a detection aptamer specific for said molecule. The ELISA assay is based on the use of antigens or antibody labeled, for example, with enzymes, such that the complexes formed between the target antigen and the labeled antibody are enzymatically active complexes. Since one of the components, in this case the antigen, is immobilized in a carrier, the antigen:antibody complexes are immobilized to the carrier and can therefore be detected by means of the addition of a substrate specific for the enzyme. In the case of ELONA, the detection aptamer can be covalently bound to an enzyme, or it can be detected by itself by a secondary antibody specific for the aptamer that is conjugated to an enzyme. Said enzyme catalyzes the transformation of a specific substrate to produce a visible signal. This technique can be modified to exchange the enzyme for another detectable reagent, such as a fluorophore. The terms ELONA and ELASA, or enzyme-linked aptamer sorbent assay, are used interchangeably herein. In a preferred embodiment the detection of TLR-4 is performed by means of ELONA.

In an analogous manner, the terms "aptacytochemistry" and "aptahistochemistry", in the context of the present invention, refer to techniques analogous to immunocytochemistry and immunohistochemistry for the detection of TLR-4 on cells and histological sections, respectively, wherein the antibody that is used for detecting the molecule of interest, in this case TLR-4, is exchanged for an aptamer specific for said molecule. The detection aptamer can be bound covalently to an enzyme, or it can be detected by itself by a secondary antibody specific for the aptamer that is conjugated to an enzyme. Said enzyme catalyzes the transformation of a specific substrate to produce a visible signal. This technique can be modified to exchange the enzyme for another detectable reagent, such as a fluorophore. In a preferred embodiment, the detection of TLR-4 is performed by means of aptacytochemistry. In another preferred embodiment, the detection of TLR-4 is performed by means of aptahistochemistry.

Alternatively, the person skilled in the art will recognize that these techniques (ELONA, aptacytochemistry, aptahistochemistry) can be adapted for exchanging the detection antibody for a probe specific for the aptamer.

The term "flow cytometry", in the context of the present invention, refers to a cell analysis technique that involves measuring the fluorescence and light dispersion features that the cells have as they pass through a ray of light. In addition to light dispersion, if prior to analysis the cells are placed in the presence of aptamers labeled with fluorescent molecules, it is possible to evaluate which cells have antigens complementary to the aptamers used. The detection of fluorescence is performed with flow cytofluorimeters (known as "cytometers" or "FACS" (fluorescence-activated cell sorter)). This technique, like the preceding techniques, was initially developed for use with fluorescently labeled antibodies but can be readily adapted for use with the aptamer of the invention.

As the person skilled in the art will understand, a complex comprising a nucleic acid aptamer with the capability of binding specifically to and inhibiting TLR-4 and comprising a sequence selected from the group consisting of SEQ ID NO: 1 and SEQ ID NO: 2 or a functionally equivalent variant thereof and a detectable reagent is particularly advantageous for detecting TLR-4, since said detectable reagent enables the detection of the aptamer comprised in the complex when it is bound to TLR-4. The technique used for detecting TLR-4 will depend on the type of detectable reagent, being able to be techniques based, for example, on fluorimetry, colorimetry or radioactivity.

Therefore, in another aspect, the present invention relates to a complex comprising a nucleic acid aptamer with the capability of binding specifically to and inhibiting TLR-4 and comprising a sequence selected from the group consisting of SEQ ID NO: 1 and SEQ ID NO: 2 or a functionally equivalent variant thereof and a functional group for detecting TLR-4.

In a particular embodiment, the functional group is a detectable reagent.

In another particular embodiment of the in vitro uses of the invention, the detection of TLR-4 is performed by means of a method selected from the group consisting of ELONA, aptacytochemistry, aptahistochemistry and flow cytometry.

The terms "aptamer", "TLR-4", "functionally equivalent variant", "complex", "functional group", "detectable reagent", "ELONA", "aptacytochemistry", "aptahistochemistry" and "flow cytometry" have been described in detail above and their definitions and particularities are herein included by reference.

Given that the ELISA, immunocytochemical, immunohistochemical and flow cytometry techniques are well-known in the art, the person skilled in the art could make the adaptations required for exchanging the antibody for the aptamer or complex according to the invention without having to conduct undue experimentation.

B. In Vitro Uses for Inhibiting TLR-4

As described above, a nucleic acid aptamer with the capability of binding specifically to and inhibiting TLR-4 and comprising a sequence selected from the group consisting of SEQ ID NO: 1 and SEQ ID NO: 2 or a functionally equivalent variant thereof can inhibit the activity of TLR-4, reducing the levels of pro-inflammatory cytokines released as a result of the activation thereof. The present invention also contemplates in vitro uses of a nucleic acid aptamer with the capability of binding specifically to and inhibiting TLR-4 and comprising a sequence selected from the group consisting of SEQ ID NO: 1 and SEQ ID NO: 2 or a functionally equivalent variant thereof, and of a complex comprising a nucleic acid aptamer with the capability of binding specifically to and inhibiting TLR-4 and comprising a sequence selected from the group consisting of SEQ ID NO: 1 and SEQ ID NO: 2 or a functionally equivalent variant thereof and a functional group, for inhibiting TLR-4.

Therefore, in another aspect, the present invention relates to an in vitro use of a nucleic acid aptamer with the capability of binding specifically to and inhibiting TLR-4 and comprising a sequence selected from the group consisting of SEQ ID NO: 1 and SEQ ID NO: 2 or a functionally equivalent variant thereof for inhibiting TLR-4.

In another aspect, the present invention relates to an in vitro use of a complex comprising a nucleic acid aptamer with the capability of binding specifically to and inhibiting TLR-4 and comprising a sequence selected from the group consisting of SEQ ID NO: 1 and SEQ ID NO: 2 or a functionally equivalent variant thereof and a functional group, for inhibiting TLR-4.

In Vitro Methods of the Invention

A. In Vitro Methods for the Detection of TLR-4

In another aspect, the present invention relates to an in vitro method for the detection of TLR-4 in a sample, hereinafter "the first in vitro method for the detection of TLR-4 of the invention" comprising
  i) contacting said sample with a nucleic acid aptamer with the capability of binding specifically to and inhibiting TLR-4 and comprising a sequence selected from the group consisting of SEQ ID NO: 1 and SEQ ID NO: 2 or a functionally equivalent variant thereof,
  ii) separating the aptamer not bound to TLR-4, and
  iii) detecting the presence of the aptamer bound to the TLR-4 present in the sample.

In a first step, the first in vitro method for detection of the invention comprises contacting said sample with a nucleic acid aptamer with the capability of binding specifically to and inhibiting TLR-4 and comprising a sequence selected from the group consisting of SEQ ID NO: 1 and SEQ ID NO: 2 or a functionally equivalent variant thereof.

The terms "aptamer", "TLR-4" and "functionally equivalent variant" have been described in detail above and their definitions and particularities are herein included by reference.

The term "sample" or "biological sample", in the context of the present invention, refers to a cell culture or to isolated biological material from a subject. The biological sample can contain any biological material suitable for detecting the desired biomarker and can comprise cells and/or non-cellular material from the subject. The sample can be isolated from any suitable tissue or biological fluid such as, for example, blood, plasma, serum, urine, cerebrospinal fluid (CSF), heart, brain. The samples used for the detection of TLR-4 are preferably biological fluids.

Alternatively, the samples are biofluid samples. The terms "biological fluid" and "biofluid" are used interchangeably herein and refer to aqueous fluids of a biological origin. The biofluid can be obtained from anywhere (such as blood, plasma, serum, urine, bile, cerebrospinal fluid, vitreous or aqueous humor, or any bodily secretion), an exudate (such as the fluid obtained from an abscess or any other site of infection or inflammation), or the fluid obtained from a joint (such as a normal joint or a joint affected by a disease such as rheumatoid arthritis). The biofluids used for the detection of TLR-4 are preferably blood, plasma, serum or cerebrospinal fluid samples.

The aptamer according to the invention is applied on the sample in a buffer suitable for allowing the binding of the aptamer to the TLR-4 molecules that may be present in the sample. Non-limiting examples of buffers suitable for allowing the binding of the aptamer of the invention and TLR-4 include PBS, TBS, phosphate buffer and citrate buffer. Preferably, these buffers contain 1 mM $MgCl_2$. The amount of aptamer required for detecting the TLR-4 molecules present in the sample will depend on both the size of the sample and on the amount of TLR-4 present therein, and it could be readily determined by optimization methods commonly used in the art. By way of indication, the aptamer concentration is at least 1 fM, at least 10 fM, at least 100 fM, at least 1 pM, at least 10 pM, at least 100 pM, at least 1 nM, at least 10 nM, at least 100 nM, at least 1 µM, at least 10 µM, at least 100 µM or more. Preferably, the aptamer concentration is between 100 fM and 1 µM, more preferably between 1 pM and 100 nM, even more preferably between 100 pM and 1 nM.

The aptamer is incubated with the sample at a suitable temperature and for a time sufficient for allowing the binding of the aptamer to the TLR-4 molecules that may be present in the sample. The temperature is preferably between 20° C. and 37° C. By way of indication, the aptamer will be incubated with the sample for at least 5 min, at least 10 min, at least 15 min, at least, 20 min, at least 30 min, at least 60 min, at least 120 min or more.

Once the aptamer has bound to the TLR-4 molecules that may be present in the sample, in a second step the sample is washed to remove the aptamer molecules that have not bound to TLR-4.

In a third step, the presence of the aptamer bound to the TLR-4 present in the sample is detected. Since the aptamer of the invention is not by itself a detectable molecule, the step of detection is a step of indirect detection through a second detectable molecule which binds specifically to the aptamer. The detection of the aptamer bound to TLR-4 can be carried out with virtually any known antibody or reagent that binds with high affinity to the aptamer of the invention. Nevertheless, the use of an antibody specific for the aptamer, for example, polyclonal serum, hybridoma supernatant, monoclonal or humanized antibodies and fragments thereof, is preferred. Said antibody specific for the aptamer is suitably labeled with a detectable reagent. The term "detectable reagent" has been described in detail above and its definition and particularities are herein included by reference. Said reagent can be detected by means of fluorimetry or colorimetry using apparatuses suitable for the type of reagents and the type of sample, which are known by the person skilled in the art. By way of example, the sample with the aptamer bound to the TLR-4 molecules present is incubated with an antibody specific for the aptamer that is conjugated with an enzyme, in conditions similar to the conditions of incubation with the aptamer, and the TLR-4-aptamer-antibody complexes are detected with the addition of a substrate that is converted by the enzyme into a detectable product, for example, by means of fluorimetry in a fluorescence microscope or by colorimetry in a spectrophotometer. Alternatively, detection can be done in an analogous manner by means of the use of a probe specific for the aptamer suitably labeled with a detectable reagent.

The person skilled in the art will recognize that the first in vitro method of the invention can be carried out as part of detection techniques such as ELONA, ELASA, precipitation and qPCR, gel mobility shift assay, Western Blotting, surface plasmon resonance, kinetic capillary electrophoresis, fluorescence binding assay, aptahistochemistry, aptacytochemistry, fluorescence microscopy or flow cytometry.

Alternatively, the aptamer according to the invention can be bound to a functional group that is part of a complex according to the invention. Therefore, in another aspect, the present invention relates to an in vitro method for the detection of TLR-4 in a sample, hereinafter "the second in vitro method for the detection of TLR-4 of the invention", comprising
  i) contacting said sample with a complex comprising a nucleic acid aptamer with the capability of binding specifically to and inhibiting TLR-4 and comprising a sequence selected from the group consisting of SEQ ID NO: 1 and SEQ ID NO: 2 or a functionally equivalent variant thereof and a functional group,
  ii) separating the aptamer or complex not bound to TLR-4, and
  iii) detecting the presence of the complex bound to the TLR-4 present in the sample.

The terms "aptamer", "TLR-4", "functionally equivalent variant", and "sample" have been described in detail above and their definitions and particularities are herein included by reference. Likewise, the particularities of the first and second steps of the first in vitro method for detection of the invention also apply to the second in vitro method for detection of the invention and are likewise included by reference.

The third step of the second in vitro method for detection of the invention comprises detecting the presence of the complex of the invention bound to the TLR-4 present in the sample. The detection of the complex according to the invention can be carried out with virtually any known antibody or reagent that binds with high affinity to the aptamer of the invention or to the functional group. The detection of the aptamer of the invention has been described in detail in the context of the first in vitro method for detection of the invention. Likewise, in relation to the functional group, the detection can also be carried out with virtually any known antibody or reagent that binds with high affinity to said functional group. For this reason, it is particularly appropriate for the second in vitro method for detection of the invention that the functional group is a detectable reagent.

In a particular embodiment the functional group is a detectable reagent selected from the group formed by radionuclides, fluorophores, proteins and haptenes.

The terms "radionuclide", "fluorophore", "detectable protein" and "haptene" have been described in detail above and their definitions and particularities are herein included by reference.

As the person skilled in the art will understand, the detectable reagents contemplated by the present invention can be divided between the reagents which are directly detectable by themselves, such as radionuclides or fluorophores, and the reagents which are indirectly detectable, such as proteins or haptenes.

In a preferred embodiment, the detectable reagent is a radionuclide and the detection is performed by detection of the radiation emitted by the radionuclide. Said radiation will depend on the type of radionuclide, being able to be an $\alpha$ particle emission, $\beta$ particle emission or $\gamma$ type emission. For this purpose, detection techniques suitable for different radionuclides are well-known. By way of example, the emission emitted by $^{123}I$ can be detected by a gamma camera.

In another preferred embodiment, the detectable reagent is a fluorophore and the detection is performed by detection of the fluorescence emitted by the fluorophore. The use of a fluorophore requires the prior excitation thereof with a wavelength within its excitation spectrum, which causes emission at a different wavelength. The excitation and emission wavelengths of the fluorophores contemplated in the present invention are part of the state of the art. The fluorescence emitted can be detected, for example, through fluorimetry techniques by using a fluorescence spectrophotometer or a fluorescence microscope.

In another preferred embodiment, the detectable reagent is a protein. Said protein could be detected depending on the type of protein used. For example:
- an enzyme requires the addition of its specific substrate which will be detectable by colorimetry, chemiluminescence or fluorimetry;
- a fluorescent protein, like a fluorophore, requires excitation at a wavelength suitable for being detectable by fluorimetry (for example, the wavelengths included in Table 1);
- an antigen or an haptene requires an antibody or another molecule that specifically recognizes it. In order to be detected, said antibody or molecule specific for the antigen/haptene must be labeled, for example, with an enzyme, and the detection will depend on the type of labeling.

The person skilled in the art will recognize that the second in vitro method of the invention can be carried out as part of detection techniques such as ELONA, ELASA, precipitation and qPCR, gel mobility shift assay, Western Blotting, surface plasmon resonance, kinetic capillary electrophoresis, fluorescence binding assay, aptahistochemistry, aptacytochemistry, fluorescence microscopy or flow cytometry.

In a particular embodiment, the detection of TLR-4 is performed by means of fluorescence.

B. In Vitro Methods for the Inhibition of TLR-4

In another aspect, the present invention relates to an in vitro method for inhibiting TLR-4 in a sample, hereinafter "the first in vitro method for the inhibition of TLR-4 of the invention", which comprises contacting a sample comprising TLR-4 with a nucleic acid aptamer with the capability of binding specifically to and inhibiting TLR-4 and comprising a sequence selected from the group consisting of SEQ ID NO: 1 and SEQ ID NO: 2 or a functionally equivalent variant thereof, in conditions suitable for inhibiting TLR-4.

The terms "aptamer", "TLR-4", "functionally equivalent variant", "inhibition of TLR-4" and "sample" have been described in detail above and their definitions and particularities are herein included by reference.

In a particular embodiment, the TLR-4 of the sample is comprised in living cells.

The first in vitro method for the inhibition of TLR-4 of the invention comprises contacting a sample comprising TLR-4 with an aptamer according to the invention in conditions suitable for inhibiting TLR-4. To that end, the aptamer of the invention is applied on the sample and it must bind to TLR-4.

The term "conditions suitable for inhibiting TLR-4", in the context of the present invention, refers to the incubation conditions that allow the binding of the aptamer of invention to TLR-4 and the subsequent inhibition thereof. These conditions include the composition of the buffer in which the aptamer of the invention is applied on the sample, the amount of aptamer, the incubation time and the incubation temperature. Non-limiting examples of buffers suitable for allowing the binding of the aptamer of the invention to TLR-4 and the inhibition thereof include PBS, TBS, phosphate buffer and citrate buffer. Preferably, these buffers contain 1 mM $MgCl_2$. The amount of aptamer required for detecting the TLR-4 molecules present in the sample will depend both on the size of the sample and on the amount of TLR-4 present therein, and it could be readily determined by optimization methods commonly used in the art. By way of indication, the aptamer concentration is at least 1 fM, at least 10 fM, at least 100 fM, at least 1 pM, at least 10 pM, at least 100 pM, at least 1 nM, at least 10 nM, at least 100 nM, at least 1 µM, at least 10 µM, at least 100 µM or more. Preferably, the aptamer concentration is between 100 fM and 1 µM, more preferably between 1 pM and 100 nM, even more preferably between 100 pM and 1 nM.

The aptamer is incubated with the sample at a suitable temperature and for a time sufficient for allowing the binding of the aptamer to the TLR-4 molecules that may be present in the sample. The temperature is preferably between 20° C. and 37° C., more preferably 37° C. By way of indication, the aptamer will be incubated with the sample for at least 5 min, at least 10 min, at least 15 min, at least 20 min, at least 30 min, at least 60 min, at least 120 min or more.

In another aspect, the present invention relates to an in vitro method for inhibiting TLR-4 in a sample, hereinafter "the second in vitro method for the inhibition of TLR-4 of the invention", which comprises contacting a sample comprising TLR-4 with a complex comprising a nucleic acid aptamer with the capability of binding specifically to and inhibiting TLR-4 and comprising a sequence selected from the group consisting of SEQ ID NO: 1 and SEQ ID NO: 2 or a functionally equivalent variant thereof and a functional group in conditions suitable for inhibiting TLR-4.

The terms "aptamer", "TLR-4", "functionally equivalent variant", "inhibition of TLR-4", "sample" and "conditions suitable for inhibiting TLR-4" have been described in detail above and their definitions and particularities are herein included by reference.

Medical Uses of the Invention

The authors of the present invention have demonstrated that the aptamer of the invention is able to block or inhibit the volume of infarction produced in a model of stroke induced in animals used in experiments, as described in Example 4. Therefore, the capability of the aptamer of the invention of binding specifically to and inhibiting TLR-4 renders it useful from a therapeutic viewpoint. It is apparent that the therapeutic effect obtained with the aptamer of the invention can be complemented with a functional group with therapeutic activity, as described in the context of the complex of the invention. Accordingly, the present invention contemplates the medical uses of the aptamer of the invention and of the complex of the invention.

A. Medical Uses of the Aptamer of the Invention

In another aspect, the present invention relates to a nucleic acid aptamer with the capability of binding specifically to and inhibiting TLR-4 and comprising a sequence selected from the group consisting of SEQ ID NO: 1 and SEQ ID NO: 2 or a functionally equivalent variant thereof for use in medicine.

In another aspect, the present invention relates to a nucleic acid aptamer with the capability of binding specifically to and inhibiting TLR-4 and comprising a sequence selected from the group consisting of SEQ ID NO: 1 and SEQ ID NO: 2 or a functionally equivalent variant thereof for use in manufacturing a drug for the treatment of a pathology characterized by an increase in expression of TLR-4 and/or an increase in activation of TLR-4.

Alternatively, it can be expressed as the use of a nucleic acid aptamer with the capability of binding specifically to and inhibiting TLR-4 and comprising a sequence selected from the group consisting of SEQ ID NO: 1 and SEQ ID NO: 2 or a functionally equivalent variant thereof for use in the treatment of a pathology characterized by an increase in expression of TLR-4 and/or an increase in activation of TLR-4.

Alternatively, it can be expressed as an in vivo method for the treatment of a pathology characterized by an increase in expression of TLR-4 and/or an increase in activation of TLR-4 in a subject, comprising the administration to said subject of a therapeutically effective amount of a nucleic acid aptamer with the capability of binding specifically to and inhibiting TLR-4 and comprising a sequence selected from the group consisting of SEQ ID NO: 1 and SEQ ID NO: 2 or a functionally equivalent variant thereof to said subject.

According to the invention, a nucleic acid aptamer with the capability of binding specifically to and inhibiting TLR-4 and comprising a sequence selected from the group consisting of SEQ ID NO: 1 and SEQ ID NO: 2 or a functionally equivalent variant thereof binds specifically to TLR-4 on the surface of a target cell. When the aptamer of the invention is contacted with TLR-4, it inhibits its activity, resulting in a reduction or interruption in the release of pro-inflammatory cytokines such as IL-1, IL-8, TNF-alpha and IL-12.

The term "aptamer" has been described in detail in relation to the Definitions and the Aptamer specific for TLR-4 (supra) and its definitions and particularities likewise apply in the context of the complex of the invention.

The term "treatment" or "therapy", in the context of the present invention, refers to the clinical intervention in an attempt to prevent, cure, delay, reduce the seriousness of, or improve one or more symptoms of the pathology characterized by an increase in expression of TLR-4 and/or an increase in activation of TLR-4, or for the purpose of prolonging survival of a patient beyond what is expected in the absence of such treatment.

The term "target cell", in the context of the present invention, refers to the particular cell that expresses TLR-4, including, inter alia, myeloid lineage cells such as monocytes, macrophages, microglia cells, granulocytes and immature dendritic cells, as well as cells of other lineages such as neurons, etc. In a particular embodiment, the target cell is a monocyte or a macrophage. In another particular embodiment, the target cell is a microglia cell. In another particular embodiment, the target cell is a granulocyte. In another particular embodiment, the target cell is an immature dendritic cell. In another particular embodiment, the target cell is a neuron.

In a particular embodiment, the target cell is a mammal cell. In another preferred embodiment, the mammal cell is a human cell.

The term "subject" or "individual" refers to a member of a mammal species, and includes, but is not limited to, domestic animals and primates, including humans; the subject is preferably a male or female human of any age or race.

The term "a therapeutically effective amount", in the context of the present invention, refers to the amount of the aptamer of the invention required for achieving a prevention, cure, delay, reduction of the seriousness of, or improvement of one or more observable symptoms of the pathology characterized by an increase in expression of TLR-4 and/or an increase in activation of TLR-4.

The term "pathology characterized by an increase in expression of TLR-4 and/or an increase in activation of TLR-4", in the context of the present invention, refers to a pathology in which the cells that express TLR-4 show an increase in expression of TLR-4 and/or an increase in activation of TLR-4, and/or a pathology in which there is an increase in the amount of cells that express TLR-4, with respect to normal or reference physiological conditions or reference values, and in which said cells are directly or indirectly involved regardless of whether or not TLR-4 is responsible for the disease. Given that activation of TLR-4 produces a signaling cascade resulting in the release of inflammatory cytokines such as IL-1, IL-8, TNF-alpha and IL-12, causing inflammation and cell damage, the pathology characterized by an increase in expression of TLR-4 and/or an increase in activation of TLR-4 can furthermore be characterized by having an inflammatory component.

In a particular embodiment, said pathology characterized by an increase in expression of TLR-4 and/or an increase in activation of TLR-4 is selected from the group consisting of, inter alia, stroke, acute myocardial infarction, sepsis, atherosclerosis, multiple sclerosis, rheumatoid arthritis, a retinal degenerative disease, and drug addiction.

In a preferred embodiment, said pathology characterized by an increase in expression of TLR-4 and/or an increase in activation of TLR-4 is a stroke. The term "stroke" or "cerebrovascular disease" or "cerebral infarction" or "apoplexy", in the context of the present invention, refers to a pathology characterized by a neurological deficit caused by an important decrease in cerebral blood flow, in an abnormally abrupt manner (ischemic stroke), or due to hemorrhaging caused by the rupture of a vessel of the brain (hemorrhagic stroke). In ischemic stroke, blood irrigation is lost due to the sudden and immediate interruption of blood flow due to occlusion of any of the arteries irrigating the brain mass, which generates the appearance of an infarcted area. Artery occlusion is generally due to atherosclerosis or an embolus (cerebral embolism) that comes from another location, fundamentally the heart or other arteries. In hemorrhagic stroke, the rupture of a blood vessel in the brain occurs, depriving the area of the brain that depends on that artery of blood. In addition the blood that flows out compresses brain structures, including other blood vessels, which increases the affected area by ischemia secondary to the intracerebral hemorrhage.

In a preferred embodiment, said pathology characterized by an increase in expression of TLR-4 and/or an increase in activation of TLR-4 is acute myocardial infarction. The term "acute myocardial infarction" or "infarction" or "heart attack", in the context of the present invention, refers to a pathology characterized by insufficient blood supply, with tissue damage, in an area of the heart, caused by an obstruction in one of the coronary arteries. Ischemia or deficient oxygen supply resulting from such obstruction causes angina pectoris, which if recannulated soon enough, does not cause death of heart tissue, whereas if this anoxia is maintained, the myocardium becomes injured and necrosis, i.e., infarction, ultimately occurs.

In a preferred embodiment, said pathology characterized by an increase in expression of TLR-4 and/or an increase in activation of TLR-4 is sepsis. The term "sepsis" or "septicemia", in the context of the present invention, refers to the systemic inflammatory response syndrome (SIRS) caused by a generally serious infection. This reaction of the organism occurs in response to the presence of pathogenic microorganisms in any tissue or fluid of the organism, and is caused by the action of the immune system itself, which releases pro-inflammatory substances which start up the SIRS. It is characterized by the presence of at least two of the following criteria: fever, hyperthermia, tachypnea, tachycardia and leukocytosis.

In a preferred embodiment, said pathology characterized by an increase in expression of TLR-4 and/or an increase in activation of TLR-4 is atherosclerosis. The term "atherosclerosis", in the context of the present invention, refers to a syndrome or pathology characterized by the deposition and infiltration of lipid substances in the walls of medium- and thick-sized arteries. The cells of the arterial wall interpret this deposition as an invasion and activate circulating monocytes of the immune system, which penetrate the arterial wall, are converted into macrophages and start to phagocyte LDL particles, generating an inflammatory process. Inflammation in turn causes the multiplication and migration of the smooth muscle cells of the wall, which gradually cause narrowing of the arterial diameter. The specific thickening is referred to as an atheromatous plaque. It is the most common form of arteriosclerosis. The diseases forming atherosclerosis syndrome and characterized by involvement of the arteries through atheromatous plaques, and accordingly obstruction of blood flow or ischemia, depending on the artery of the organ involved, are:

Ischemic heart disease, the maximum representative thereof being acute myocardial infarction, in the heart.

Cerebrovascular disease, in the form of stroke or cerebral thrombosis or cerebral hemorrhage, in the central nervous system.

Intermittent claudication, the maximum seriousness thereof being acute arterial ischemia of the lower limbs.

Erectile dysfunction: this is the principal cause of impotency in people over 40 years of age.

Ischemic colitis, which is an area of inflammation (irritation and swelling) caused by interference with the blood flow to the colon (large intestine), in the arteries of the intestines.

Aortic aneurism, the maximum seriousness thereof being aortic dissection.

In a preferred embodiment, said pathology characterized by an increase in expression of TLR-4 and/or an increase in activation of TLR-4 is multiple sclerosis. The term "multiple sclerosis", in the context of the present invention, refers to a pathology characterized by the onset of demyelinating, neurodegenerative and chronic lesions of the central nervous system. Its causes are currently unknown, although the involvement of various autoimmune mechanisms has been demonstrated. In multiple sclerosis patients, lymphocytes cross the blood-brain barrier to affect the myelin, while an inflammatory process aided by macrophages and neuroglia cells occurs.

In a preferred embodiment, said pathology characterized by an increase in expression of TLR-4 and/or an increase in activation of TLR-4 is rheumatoid arthritis. The term "rheumatoid arthritis", in the context of the present invention, refers to a systemic autoimmune inflammatory pathology, characterized by causing persistent synovitis of the joints, causing their progressive destruction, generating different degrees of deformity and functional disability. The process starts with the intervention of humoral and cell factors, particularly CD4 T-cells, which generate inflammation mediating molecules, attract and activate peripheral blood cells, causing proliferation and activation of the synoviocytes, invading and destroying joint cartilage, subchondral bone, tendons and ligaments.

In a preferred embodiment, said pathology characterized by an increase in expression of TLR-4 and/or an increase in activation of TLR-4 is a retinal degenerative disease. The term "retinal degenerative disease", in the context of the present invention, refers to a disease or disorder characterized by a degeneration of the retina, which may be the result of retinal inflammation. TLR-4-mediated microglial activation has been shown to make a contribution to the process of retinal inflammation. Major retinal degenerative diseases include:

Age-related macular degeneration (AMD), which results in a loss of vision in the center of the visual field (the macula) because of damage to the retina. It occurs in "dry" and "wet" forms: in the dry (nonexudative) form, cellular debris called drusen accumulates between the retina and the choroid, causing atrophy and scarring to the retina; in the wet (exudative) form, which is more severe, blood vessels grow up from the choroid behind the retina which can leak exudate and fluid and also cause hemorrhaging.

Stargardt disease, or fundus flavimaculatus, is an inherited form of juvenile macular degeneration that causes progressive vision loss usually to the point of legal blindness. The onset of symptoms usually appears between the ages of 6 and 13 years old (average of about 16-18 years). Symptoms typically develop by 20 years of age, and include wavy vision, blind spots, blurriness, impaired color vision, and difficulty adapting to dim lighting.

Retinitis pigmentosa (RP), which is an inherited, degenerative eye disease that causes severe vision impairment due to the progressive degeneration of the rod photoreceptor cells in the retina. Patients in the early stages of RP first notice compromised peripheral and dim light vision due to the decline of the rod photoreceptors. The progressive rod degeneration is later followed by abnormalities in the adjacent retinal pigment epithelium and the deterioration of cone photoreceptor cells. As peripheral vision becomes increasingly compromised, patients experience progressive "tunnel vision" and eventual blindness.

Other genetic diseases such as choroideremia, Leber congenital amaurosis, retinoschisis juvenile, Usher disease, and Bardet Biedl.

In a particularly preferred embodiment, the retinal degenerative disease is selected from the group consisting of AMD, Stargardt disease, RP, choroideremia, Leber congenital amaurosis, retinoschisis juvenile, Usher disease, and Bardet Biedl. In a more preferred embodiment, the retinal degenerative disease is AMD. In another more preferred embodiment, the retinal degenerative disease is Stargardt disease. In another more preferred embodiment, the retinal degenerative disease is RP. In another more preferred embodiment, the retinal degenerative disease is choroideremia. In another more preferred embodiment, the retinal degenerative disease is Leber congenital amaurosis. In another more preferred embodiment, the retinal degenerative disease is Usher disease. In another more preferred embodiment, the retinal degenerative disease is Bardet Biedl.

In a preferred embodiment, said pathology characterized by an increase in expression of TLR-4 and/or an increase in activation of TLR-4 is a drug addiction. The term "drug addiction" or "drug dependence", in the context of the present invention, refers to a disorder or pathology caused by the frequent use of addictive substances called drugs. According to ICD-10 (World Health Organization, 2005), in order to be diagnosed as such, the drug dependence must present three or more of the following criteria, which refer both to aspects related to physical dependence and to psychological dependence, in a 12-month period:

strong craving to consume the substance,
difficulties in controlling said consumption,
withdrawal syndrome when consumption is discontinued or reduced,
tolerance,
progressive abandonment of interests other than substance consumption,
increase in time invested in activities related to obtaining the substance or to recovering from its effects,
persistence in the use of the substance despite clearly perceiving its harmful effects.

For the administration to a subject of a nucleic acid aptamer with the capability of binding specifically to and inhibiting TLR-4 and comprising a sequence selected from the group consisting of SEQ ID NO: 1 and SEQ ID NO: 2 or a functionally equivalent variant thereof, said aptamer will be formulated in a suitable pharmaceutical composition. The details of said pharmaceutical composition are discussed below.

B. Medical Uses of the Complex of the Invention

The complexes according to the present invention comprising a nucleic acid aptamer with the capability of binding specifically to and inhibiting TLR-4 and comprising a sequence selected from the group consisting of SEQ ID NO: 1 and SEQ ID NO: 2 or a functionally equivalent variant thereof and a functional group according to the invention can comprise, as a functional group, a drug suitable for the treatment of a pathology characterized by an increase in expression of TLR-4 and/or an increase in activation of TLR-4. The dual objective of (i) inhibiting the activity of TLR-4 and (ii) directing the drug in a specific manner to its site of action, is therefore achieved.

Therefore, in another aspect, the present invention refers to a complex comprising a nucleic acid aptamer with the capability of binding specifically to and inhibiting TLR-4 and comprising a sequence selected from the group consisting of SEQ ID NO: 1 and SEQ ID NO: 2 or a functionally equivalent variant thereof and a functional group for use in medicine.

In another aspect, the present invention relates to a complex comprising a nucleic acid aptamer with the capability of binding specifically to and inhibiting TLR-4 and comprising a sequence selected from the group consisting of SEQ ID NO: 1 and SEQ ID NO: 2 or a functionally equivalent variant thereof and a functional group for use in manufacturing a drug for the treatment of a pathology characterized by an increase in expression of TLR-4 and/or an increase in activation of TLR-4.

Alternatively, it can be expressed as the use of a complex comprising a nucleic acid aptamer with the capability of binding specifically to and inhibiting TLR-4 and comprising a sequence selected from the group consisting of SEQ ID NO: 1 and SEQ ID NO: 2 or a functionally equivalent variant thereof and a functional group for use in the treatment of a pathology characterized by an increase in expression of TLR-4 and/or an increase in activation of TLR-4.

Alternatively, it can be expressed as method of treatment of a pathology characterized by an increase in expression of TLR-4 and/or an increase in activation of TLR-4 in a subject, comprising the administration to said subject of a therapeutically effective amount of a complex comprising a nucleic acid aptamer with the capability of binding specifically to and inhibiting TLR-4 and comprising a sequence selected from the group consisting of SEQ ID NO: 1 and SEQ ID NO: 2 or a functionally equivalent variant thereof and a functional group to said subject.

According to the invention, a complex comprising a nucleic acid aptamer with the capability of binding specifically to and inhibiting TLR-4 and comprising a sequence selected from the group consisting of SEQ ID NO: 1 and SEQ ID NO: 2 or a functionally equivalent variant thereof and a drug binds specifically to TLR-4 in the surface of a target cell. When the aptamer of the invention is contacted with TLR-4, it inhibits its activity, resulting in a reduction or interruption in the release of pro-inflammatory cytokines such as IL-1, IL-8, TNF-alpha and IL-12, and the drug exerts its function on the cell or on the environment where said cell is located.

The terms "aptamer", "TLR-4", "functionally equivalent variant", "complex", "functional group", "drug", "treatment", "therapeutically effective amount", "subject", "target cell" and "pathology characterized by an increase in expression of TLR-4 and/or an increase in activation of TLR-4" have been described in detail above and their definitions and particularities are herein included by reference.

Suitable drugs that can be used as functional groups in the complexes formed with a nucleic acid aptamer with the capability of binding specifically to and inhibiting TLR-4 include, without limitation, antagonists of TLR-4, such as naloxone, naltrexone, LPS, ibudilast, propentofylline, amitriptyline, ketotifen, cyclobenzaprine, mianserin and imipramine; anti-platelet drugs, such as aspirin and clopidogrel; anti-coagulants, such as heparin, acenocumarol, warfarin, dabigatran and rivaroxaban; and antioxidants, such as edaravone; the tissue plasminogen activator and the recombinant variants thereof; nucleic acids which have the capability of silencing the expression of genes involved in a pathology characterized by an increase in expression of TLR-4 and/or an increase in activation of TLR-4, such as antisense RNA, antisense DNA and small interfering RNA; peptides, such as signaling peptides and target-binding peptides.

Pharmaceutical Compositions

For the administration to a subject in need of a nucleic acid aptamer with the capability of binding specifically to and inhibiting TLR-4 and comprising a sequence selected from the group consisting of SEQ ID NO: 1 and SEQ ID NO: 2 or a functionally equivalent variant thereof, or a complex comprising a nucleic acid aptamer with the capability of binding specifically to and inhibiting TLR-4 and comprising a sequence selected from the group consisting of SEQ ID NO: 1 and SEQ ID NO: 2 or a functionally equivalent variant thereof and a functional group, said aptamers and complexes can be formulated in suitable pharmaceutical compositions.

In another aspect, the present invention relates to a pharmaceutical composition, hereinafter "the first pharmaceutical composition of the invention", comprising at least one nucleic acid aptamer with the capability of binding specifically to and inhibiting TLR-4 and comprising a sequence selected from the group consisting of SEQ ID NO: 1 and SEQ ID NO: 2 or a functionally equivalent variant thereof.

In a particular embodiment, the first pharmaceutical composition of the invention further comprises one or more pharmaceutically acceptable carriers, excipients, or solvents.

In another aspect, the present invention relates to a pharmaceutical composition, hereinafter "the second pharmaceutical composition of the invention", comprising at least one complex comprising a nucleic acid aptamer with the capability of binding specifically to and inhibiting TLR-4 and comprising a sequence selected from the group consisting of SEQ ID NO: 1 and SEQ ID NO: 2 or a functionally equivalent variant thereof and a functional group.

In a particular embodiment, the second pharmaceutical composition of the invention further comprises one or more pharmaceutically acceptable carriers, excipients, or solvents.

The pharmaceutical compositions provided by the present invention can be administered to a subject for the treatment of a pathology characterized by an increase in expression of TLR-4 and/or an increase in activation of TLR-4.

The terms "aptamer", "TLR-4", "functionally equivalent variant", "complex", "functional group", "drug", "treatment", "subject" and "pathology characterized by an increase in expression of TLR-4 and/or an increase in activation of TLR-4" have been described in detail above and their definitions and particularities are herein included by reference.

The term "pharmaceutically acceptable carrier" or "pharmaceutically acceptable excipient" or "pharmaceutically acceptable solvent", in the context of the present invention, seeks to include any and all of the solvents, dispersion media, coatings, antibacterial and antifungal agents, absorption delaying and isotonic agents, and the like, compatible with the pharmaceutical administration. The use of such carriers and vehicles in pharmaceutically active substances is well-known in the art. Unless any conventional carrier is incompatible with the active compound, use thereof in the compositions of the invention is contemplated. The acceptable vehicles, excipients, or acceptable stabilizers are not toxic for the subject at the doses and concentrations used, and include buffers such as phosphate, citrate, and other organic acids; antioxidants including ascorbic acid and methionine; preservatives (such as octadecyldimethylbenzyl ammonium chloride, hexamethonium chloride, benzalkonium chloride, benzethonium chloride; phenol, butyl or benzyl alcohol; alkyl parabens such as methyl or propyl paraben; catechol; resorcinol; cyclohexanol; 3-pentanol, and m-cresol); low molecular weight polypeptides (less than about 10 amino acids); proteins, such as serum albumin, gelatin, or immunoglobulins; hydrophilic polymers such as polyvinylpyrrolidone; amino acids such as glycine, glutamine, asparagine, histidine, arginine or lysine; monosaccharides, disaccharides, and other carbohydrates including glucose, mannose, or dextrins; chelating agents such as EDTA; sugars such as sucrose, mannitol, trehalose or sorbitol; salt-forming counterions such as sodium; metal complexes (for example, Zn-protein complexes); and/or non-ionic surfactants such as TWEEN™, PLURONICS™ or polyethylene glycol (PEG).

Supplementary active compounds can also be incorporated in the pharmaceutical composition provided by the present invention. Therefore, in a particular embodiment, the pharmaceutical composition provided by the present invention can also contain more than one active compound as required for the particular indication in question, preferably those with complementary activities that do not adversely affect one another. For example, it may desirable to furthermore provide a chemotherapeutic agent, a cytokine, an analgesic agent, an anti-inflammatory agent or an immunosuppressive agent. The effective amount of said other active agents depends, among other things, on the therapeutic amount of the aptamers or of the complexes which are present in the pharmaceutical composition, the nature and the seriousness of the pathology to be treated, the subject, etc.

In one embodiment, the nucleic acid aptamer with the capability of binding specifically to and inhibiting TLR-4 and comprising a sequence selected from the group consisting of SEQ ID NO: 1 and SEQ ID NO: 2 or a functionally equivalent variant thereof, or the complex of the invention, are formulated with vehicles that will protect said products from rapid elimination from the body, such as a controlled release formulation, including implants and microencapsulated delivery system. Biodegradable and biocompatible polymers, such as ethylene-vinyl acetate, polyanhydrides, polyglycolic acid, collagen, polyorthoesters, and polylactic acid can be used. The methods for the preparation of such formulations will be evident for persons skilled in the art.

These can be prepared according to methods known by persons skilled in the art, for example, as described in U.S. Pat. No. 4,522,811.

The pharmaceutical compositions provided by the present invention can be administered to a subject by means of any suitable administration route, such as, for example, by parenteral route.

The term "parenteral", in the context of the present invention, includes the intravenous, intraperitoneal, intramuscular, or subcutaneous administration. The intravenous form of parenteral administration is generally preferred.

Furthermore, the pharmaceutical compositions provided by the present invention can be suitably administered by pulse infusion, for example, with decreasing does of the aptamer or of the complex of the invention. Preferably, the dosage is provided by means of injections, more preferably intravenous or subcutaneous injections, depending in part on whether the administration is brief or chronic.

In another particular embodiment, the pharmaceutical compositions provided by the present invention can be adapted for parenteral administration with the addition of sterile solutions, suspensions or lyophilized products in the suitable dosage form. The pharmaceutical compositions suitable for injectable use include sterile aqueous solutions or dispersions or sterile powders for the preparation of sterile injectable solutions or dispersions. For intravenous administration, suitable vehicles include physiological saline solution, bacteriostatic water CremophorEM (BASF, Parsippany, N.J.) or phosphate buffer saline (PBS). In all cases, the composition must be sterile and fluid to facilitate injectability. It must be stable in the manufacturing and storage conditions and must be preserved against the contaminating action of microorganisms such as bacteria and fungi. The vehicle can be a solvent or dispersion medium which contains, for example, water, ethanol, a pharmaceutically acceptable polyol such as glycerol, propylene glycol, liquid polyethylene glycol, and suitable mixtures thereof. Suitable fluidity can be maintained, for example, by means of the use of a coating such as lecithine, by means of maintaining the particle size required in the case of dispersion and by the use of surfactants. The prevention of the action of microorganisms can be achieved by means of various antibacterial and antifungal agents, for example, parabens, chlorobutanol, phenol, ascorbic acid, thimerosal, and the like. In many cases, it will be preferable to include in the composition isotonic agents, for example, sugars, polyalcohols such as mannitol, sorbitol, and sodium chloride. The prolonged absorption of the injectable compositions can be provoked, including in the composition an absorption-delaying agent, for example, aluminum monostearate and/or gelatin.

The injectable sterile solutions can be prepared by incorporating the required amount of the active compound (for example, an aptamer or complex of the invention) in a suitable solvent with one or a combination of the previously listed ingredients, as required, followed by filtration sterilization. Generally, the dispersions are prepared by incorporating the active compound in a sterile vehicle which contains a basic dispersion medium and the other required ingredients from those previously listed. In the case of sterile powders for the preparation of injectable sterile solutions, the preferred methods of preparation are vacuum-drying and freeze-drying, which produces a powder of the active ingredient plus any additional desired ingredient from previously filtered sterile solution thereof.

In a particular embodiment, said pharmaceutical composition is administered through intravenous route. Suitable excipients, such as bulking agents, buffering agents or surfactants, can be used. The mentioned formulations will be prepared using standard methods such as those described or contemplated in the Spanish and United States pharmacopoeias and similar reference texts.

It is particularly advantageous to formulate the pharmaceutical compositions, namely, the parenteral compositions, in the dosage unit form to facilitate the dosage administration and uniformity. Dosage unit form, as it is used herein, refers to physically discrete units suitable as unit dosages for the subject to be treated, each unit containing a predetermined amount of active compound (an aptamer or complex of the invention) calculated to produce the desired therapeutic effect in association with the required pharmaceutical vehicle. The specification for the unit dosage forms of the invention are conditioned by and depend directly on the unique features of the active compound and the particular therapeutic effect to be achieved, and the inherent limitations in the composition technique of such active compound for the treatment of subjects.

The active compounds (aptamer or complex of the invention) will typically be administered one or more times a day, for example 1, 2, 3 or 4 times a day, with typical total daily doses in the interval of 0.0001 to 1.000 mg/kg of body weight/day, preferably from about 0.001 to about 100 mg/kg of body weight/day, more preferably from about 0.01 to 10 mg/kg of body weight/day. The pharmaceutical compositions can be formulated for the purpose of containing the desired amount, such as a therapeutically effective amount of the aptamer or complex of the invention.

The pharmaceutical compositions provided by the present invention can be included in a container, packaging, or dispenser together with instructions for administration.

Imaging Methods of the Invention

In another aspect, the invention relates to the use of a complex according to the invention for in vivo imaging of a cell, tissue or organ which express TLR4, wherein said complex comprises one or more aptamers according to the invention and a functional group, said functional group being a detectable moiety.

Suitable detectable moieties for use in the in vivo imaging methods according to the invention have been described above in the context of the complex of the invention and include, without limitation, a radionuclide, a fluorophore, a contrast media, a protein and an haptene.

The invention is described below by means of the following examples which are merely illustrative and by no means limiting of the scope of the invention.

EXAMPLES

Materials and Methods

Aptamer Library

The inventors used the RND40 aptamer library to carry out the screening of aptamers specific for TLR-4, supplied by IBA GmbH (Goettingen, Germany). The initial RND40 library is theoretically made up of $10^{24}$ single-stranded DNA (ssDNA) oligonucleotides with fixed sequence at the ends, consisting of 18 nucleotides where each hybridize the respective primers for PCR amplification thereof, and a central region consisting of 40 bases having random sequence. In the screenings made, $10^{13}$ oligonucleotides from this library have been used.

6HIS-recombinant hTLR-4

The protein corresponding to the extracellular domain of the human TLR-4 protein, amino acids 24-631, was recombinantly generated fused to a 6-histidine tag at the C-terminal end, by means of expression in baculovirus.

Cells

HEK293T and HEK293T/TLR-4 cells were obtained from Invivogen (San Diego, Calif., USA).

Screening with HEK-293T-TLR4/HEK-293T Cells

For each screening round, 8-10×10$^5$ HEK-293T cells were seeded in triplicate in P6 plate wells, 24 h before the screening assay and were incubated at 37° C., 5% $CO_2$. Then 1 nmol of aptamers from the RND40 library (or from the population isolated in the preceding screening round) in 100 μl PBS, which aptamers were previously denatured at 95° C. for 10 min followed by incubation at 4° C. for 10 min, was added; 300 μl of DMEM medium (Dulbecco's modified Eagle's medium) supplemented with 10% fetal bovine serum, 100 U/ml penicillin, 100 μg/ml streptomycin and 25 μg/ml amphotericin were added and applied on the cells. After 1 h of incubation at 37° C., 5% $CO_2$, the culture medium with the non-bound aptamers was removed, the cells were washed twice with PBS and recovered in 500 μl of PBS by means of centrifugation at 1500 rpm. The cells were centrifuged to remove the supernatant and the aptamers adhered to the cells were amplified by PCR to prepare a sufficient amount for the following screening round.

The counter-screening on HEK-293T cells from the RND40 aptamer library was done during the prior preparation of the initial RND40 population and every 3 screening rounds, with the population isolated from the preceding screening round. To that end, 8-10×10$^5$ HEK-293T cells were seeded in triplicate in P6 plate wells, 24 h before the screening assay and were incubated at 37° C., 5% $CO_2$. Then, 1 nmol of aptamers of the RND40 library (or of the population isolated in the preceding screening round) in 100 μl PBS, which aptamers were previously denatured at 95° C. for 10 min followed by incubation at 4° C. for 10 min, was added; 300 μl of DMEM medium (Dulbecco's modified Eagle's medium) supplemented with 10% fetal bovine serum, 100 U/ml penicillin, 100 μg/ml streptomycin and 25 μg/ml amphotericin were added and applied on the cells. After 1 h of incubation at 37° C., 5% $CO_2$, the culture medium with the non-bound aptamers for being used in screening rounds on TLR-4 was removed.

Screening with Soluble hTLR-4 Protein

For each screening round, the RND40 library enriched in a preceding screening round is used. 1 nmol of aptamers was incubated with 7 μg of 6×HIS-hTLR-4 (at a ratio of 10 aptamer molecules to 1 hTLR-4 molecule), in an aptamer buffer (20 mM Tris-HCl, pH 7.4, 1 mM $MgCl_2$, 150 mM NaCl, 5 mM KCl), at 37° C. for 1 h with stirring. Subsequently, NTA-Ni resin (QIAGEN, Germany) was added and it was incubated at 4° C. for 1 h to capture the protein. After 3 washes with aptamer buffer, the bound sequences were amplified by PCR to prepare a sufficient amount for the following screening round.

The counter-screening is performed in the same conditions as screening but in the absence of TLR-4 protein bound to the resin.

Amplification of the Selected Aptamers

The selected aptamers were resuspended in a volume of 20 μl of distilled water and amplified by means of PCR using the primers, which will correspond with sequences SEQ ID NO: 5 (GCGGATGAAGACTGGTGT) and SEQ ID NO: 6 (GTTGCTCGTATTTAGGGC) in the conditions of 0.8 μM/primer SEQ ID NO: 5, 0.8 μM/primer SEQ ID NO: 6, 200 mM dNTPs, 2 mM $MgCl_2$, 10 U Taq polymerase (Biotools, Spain) in a final volume of 200 μl according to the following amplification program: 2 min at 95° C.; 15 cycles of 30 s at 95° C., 30 s at 56° C. and 30 s at 72° C.; and finally 5 min at 72° C.

ELONA

It was determined if the selected aptamers recognized the TLR-4 protein. To that end, 100 ng/well of 6×HIS-recombinant TLR-4 were added to a 96-well microtiter plate and were incubated at 4° C. for 16 h. Subsequently, individual aptamers labeled with digoxigenin in the 5' end were diluted at a concentration of 5 μg/mL and then denatured for 10 min at 95° C. and cooled for 10 min on ice. Then, 20 pmol of each of the aptamers in 100 μl (200 nM) of aptamer buffer were added to each well and the plate was incubated for 1 h at 37° C. Finally, the plate was incubated with peroxidase-conjugated anti-digoxigenin antibodies and developed using ABTS. An anti-Li H2A DNA aptamer was used as a positive control (Martin et al., 2013, PLoS ONE 8: e78886).

Binding Assays for Binding the Aptamers to Recombinant hTLR-4

For the purpose of analyzing the capability of each of the identified aptamers of binding to hTLR-4, experiments were performed in which hTLR-4 was bound to a Ni-NTA resin, previously equilibrated, through the histidine tag. Then, the resin:protein complexes containing 1 pmol of TLR4 were incubated with 1 pmol of aptamers TLRApt #1R (SEQ ID NO: 3), TLRApt #2F, TLRApt #3R and TLRApt #4F (SEQ ID NO: 4), previously structured by means of thermal denaturation at 95° C. for 10 min and subsequent renaturation at 4° C. for 10 min. After incubating for 10 min at 37° C., the complexes were washed and the aptamers were recovered with 150 mM imidazol dissolved in PBS with 1 mM $MgCl_2$. The values of aptamer bound to hTLR-4 were determined by means of quantitative PCR (qPCR) using the primers with sequences SEQ ID NO: 5 and SEQ ID NO: 6 in an IQ5 thermal cycler (BioRad).

Binding Assays for Binding the Aptamers to TLR-4 Expressed in Cells

For the purpose of analyzing the capability of the identified aptamers of binding to the TLR-4 protein expressed in HEK-293 cells, 20 pmol of each of the aptamers TLRApt #1R (SEQ ID NO: 3), TLRApt #2F, TLRApt #3R and TLRApt #4F (SEQ ID NO: 4) were added to a HEK-293-TLR4 cell culture seeded at 20,000 cells/well in 96-well microtiter plates at a density of 2×10$^4$ cells/well, 2 days before the start of the assay. After incubating for 30 min at 37° C., 5% $CO_2$, the cells were washed, the aptamers were recovered with 150 mM imidazol dissolved in PBS with 1 mM $MgCl_2$, and qPCR was carried out to determine the values of Ct.

Receptor hTLR-4 Activity Assays

To perform these assays, HEK-Blue hTLR4 cells (Invivogen, ref. hkb-ht1r4), expressing human receptor TLR-4, together with the MD2 and CD14 proteins, which are activated by the binding of their agonist, lipopolysaccharide from *Escherichia coli* K12 (LPS-EK), were used. For detecting activation of TLR-4, this cell line contains a SEAP (secreted embryonic alkaline phosphatase) reporter gene, which is controlled by the NF-κB promoter, such that it is expressed in response to this NF-κB signaling route, induced by TLR-4. The SEAP enzyme is secreted into the culture medium, and by adding and metabolizing its commercial substrate QUANTI-Blue™ (Invivogen, San Diego, Calif., USA) it causes a change in color of the medium from red to blue. In addition, the control agonist molecule LPS-EK UP (lipopolysaccharide from *E. coli* K12, Ultra Pure) and antagonist LPS-RS UP (lipopolysaccharide from *R. sphaeroides*, Ultra Pure) are dissolved in 1 mM $MgCl_2$ in sterile PBS at concentrations of 0.02 ng/μL and 2 ng/μL, respectively. The aptamers are prepared at concentrations of 0.1, 1, 10 and 100 ng/μL in 1 mM $Cl_2Mg$ in sterile PBS, are denatured at 95° C. for 10 min and were structured at 4° C. for 10 min.

For the assay, HEK Blue-hTLR4 cells were seeded onto 96-well culture plates at $2\times10^4$ cells/well in 200 μL complete medium DMEM supplemented with (1×) HEK-Blue™ Selection. After 24 h or 48 h incubation, when the cells get 70-80% confluence, the medium is recovered and added 170 μL fresh medium. In control wells 30 μL SELEX buffer is added. In the other wells, 20 μL of LPS-EK-ultra pure (Invivogen, USA) at 20 ng/mL (0.1 ng/mL final) or 20 μL of lysate from 1.5–2.5×107 HEK293 cells/mL (Damage-associated molecular pattern; DAMP) were added as agonist molecules. After 1 h incubation, 10 μL aptamer diluted in SELEX buffer to the appropriate concentrations were added to the wells to reach final concentrations indicated in the figures. LPS-RS ultra-pure (Invivogen, USA) at a concentration of 200 ng/mL was used as antagonist control. Secreted embryonic alkaline phosphatase (SEAP) activity was measured after 24 h using QUANTI-Blue™ substrate (Invivogen) at 630 nm.

Effect of Aptamers on Macrophages

Peritoneal macrophages were seeded in 12-well plates at a density of $1\times10^6$ cells/ml. Macrophages were stimulated in the presence of 500 ng/ml LPS and 1 h after the aptamer was added to a final concentration of 20 nM and 200 nM. Nitrites release was measured by the Griess reaction after 24 h. Samples were assayed in duplicate.

Animal Model of Stroke

Adult male C57BL mice weighing 28 to 30 g were used. C57BL/10ScNJ (formerly called C57BL/10ScCr) and C57BL/10ScSn mice were acquired from The Jackson Laboratory (Bar Harbor, Me., USA). The murine strain C57BL/10ScNJ does not express functional TLR4 by deletion of the TLR4 gene, and the C57BL/10ScSn strain does not express any mutation in the TLR4 gene and is used as a control group. 4 TLR4-deficient mice were used per group (C57BL/10ScNJ) and 4 control mice were used per group (C57BL/10ScSn). All the experimental protocols complied with the guidelines of the "Comité de Bienestar Animal" (Animal Well-being Committee) of the Universidad Complutense (following European Directives 86/609/EEC and 32/2007/EC). The animals were housed in normal temperature conditions, moisture conditions and 12-hour light/darkness cycle conditions with free access to food and water.

The induction of focal cerebral ischemia was carried out by means of median cerebral arterial occlusion (MCAO) according to the teachings of Caso et al., 2007 (Caso et al., 2007, Circulation 115:1599-608). Briefly, permanent focal cerebral ischemia is induced by ligature of the common carotid artery (CCA) and distal ipsilateral occlusion of the median cerebral artery (MCA). For the ligature of the CCA, a ventral-cervical incision is made to isolate said artery and occlude it permanently via ligature. For occlusion of the MCA, an incision is made at 1 cm of the perpendicular line joining the lateral cantus of the left eye and the outer ear canal and the temporal muscle is removed. A drill hole is made to expose the MCA that is occluded by ligature. After surgery, closure of the incisions and disinfection, the animals are returned to their cages with free access to water and food. The animal's vital signs are controlled during surgery.

Brain damage was evaluated by means of magnetic resonance imaging. Briefly, the mice were anesthetized with isoflurane and 24 hours after MCAO, the size of the infarction was evaluated by MRI. The images highlighted in T2 (T2W1) were acquired in a BIOSPEC BMT 47/40 operating at 4.7 T (Bruker-Medical, Ettlingen, Germany; MRI Unit, Instituto Pluridisciplinar, UCM).

Flow Cytometry Analysis

All flow cytometry analyses were performed on a FACScan model flow cytometer (Becton Dickinson Immunocytometry systems). Binding of aptamers to cell surface TLR4 was analyzed by seeding HEK293 or HEK Blue-hTLR4 cells onto 24-well culture plates at $2\times10^5$ cells/well in 200 μL complete medium DMEM supplemented with HEK-Blue™ Selection buffer. Afterwards, cells are treated or not with the TLR-4 activator LPS-EK-UP (0.4 ng/well) for 30 min and then with the Alexa Fluor 488-labelled aptamers (20 nM) in 50 μL volume of PBS buffer containing 1 mM $MgCl_2$ and 1 mg/ml BSA for 30 min at room temperature in the dark. Cells were then washed with 2 mL of the same buffer, suspended in 0.5 mL of the buffer and subjected to flow cytometry analysis.

Nucleases Digestion

Three hundred ng of aptamers were folded in SELEX buffer by heating to 95° C. and cooling on ice. Refolded aptamer were incubated with 2 U of λ Exonuclease or DNAse I (Fermentas) in a 10 μL reaction for 10 min, 30 min, 1 h, 2 h and 4 h at 37° C. Afterward, samples were solved on a 3% agarose gel. Bands were visualized by GelRed (Biotium) and quantified using Image Studio Digits V3.1 software.

Example 1

Screening of Aptamers Specific for TLR-4

The inventors used the RND40 aptamer library to carry out the screening of aptamers specific for TLR-4 supplied by IBA GmbH (Goettingen, Germany). The initial RND40 library is made up of oligonucleotides (ssDNA) with fixed sequence at the ends, consisting of 18 nucleotides each, where they hybridize the respective primers for PCR amplification thereof, and a central region consisting of 40 bases having a random sequence.

The initial RND40 library of $10^{13}$ aptamers was enriched in aptamers specific for hTLR-4. As a prior step to screening with TLR-4, a "counter-screening" process was performed on the library for the surface or matrix where the target molecule (magnetic resin, cells of the same line as that which expresses the target protein, etc.) is presented.

Example 2

Characterization of the Selected Aptamers

The selected aptamers were identified after 6 screening rounds according to the following strategies:
 a) By means of cloning of the population of aptamers into a plasmid for the purpose of obtaining individual aptamers, and subsequent Sanger sequencing.
 b) By means of massive sequencing of the population of aptamers obtained the aptamers that are the most repeated being identified.

The sequences that are most represented were chemically synthesized by IBA GmbH (Goettingen, Germany) and the affinity and activity of each of the aptamers was studied in binding assays for binding to recombinant hTLR-4 protein or to HEK-293 cells-TLR-4, by means of ELONA, binding assays for the binding of the aptamers to the recombinant TLR-4 protein and to TLR-4 expressed in cells, receptor hTLR-4 activity assays.

Figure 2:
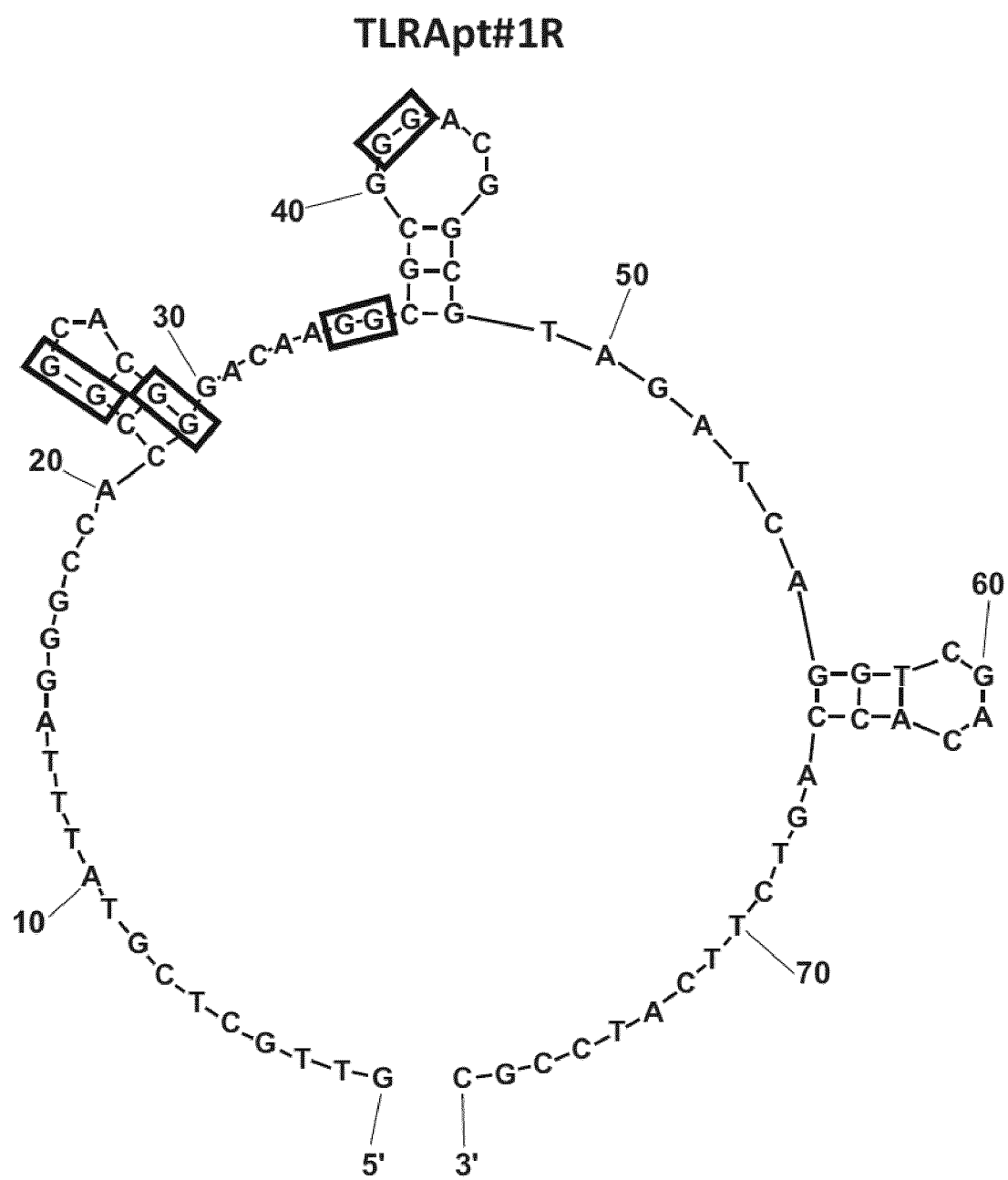
FIG. 2. Secondary structures of the aptamers TLRApt #1R (SEQ ID NO: 3) and TLRApt #4F (SEQ ID NO: 4) predicted using the mFold program. The guanines that could be part of predicted G-quadruplex structures are shown in the boxes with the QGRS Mapper program.
Figure 2:
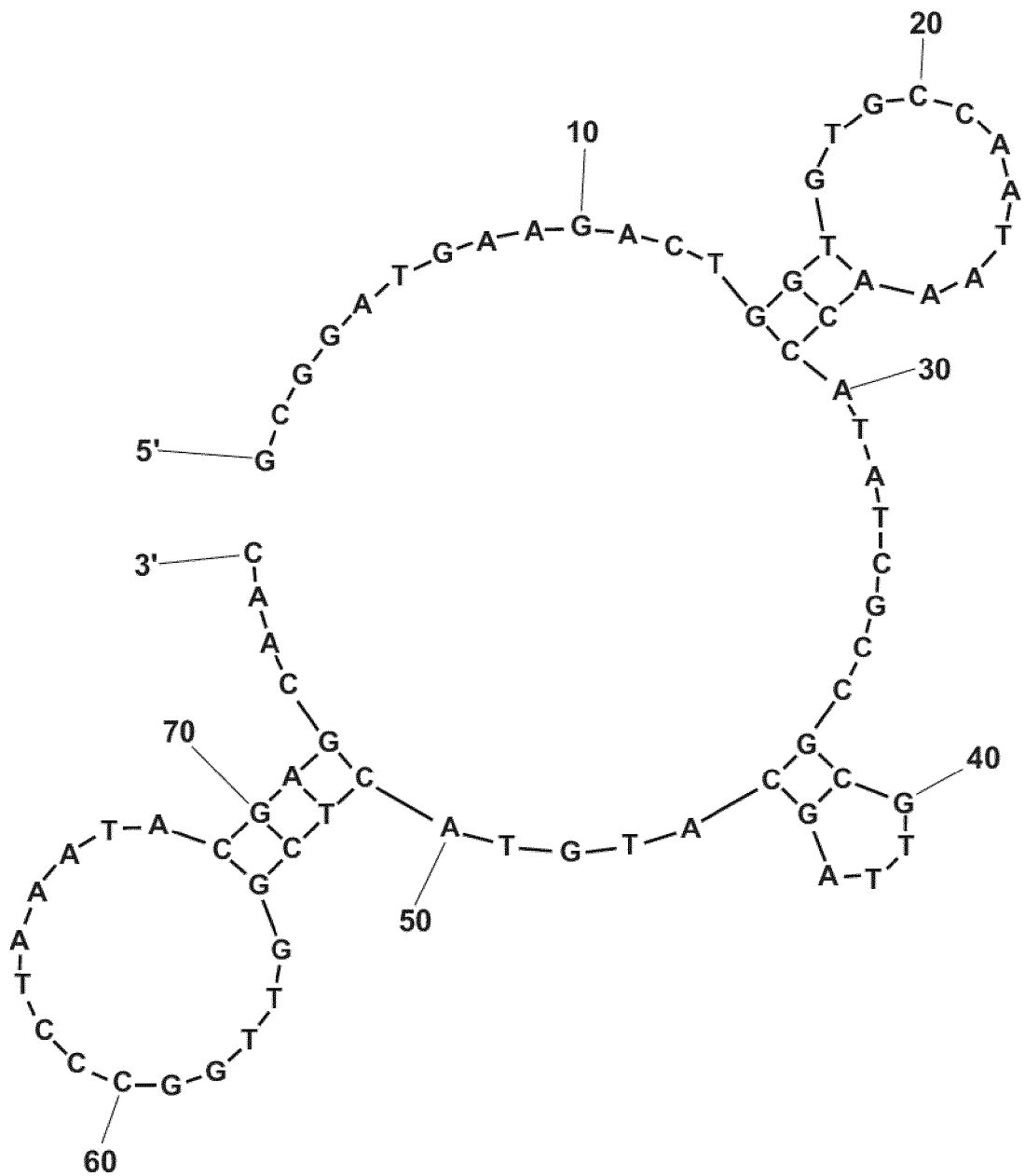

The results of the ELONA assays (FIG. 1) clearly show that the aptamers that more efficiently bind to the recombinant hTLR-4 protein are aptamers TLRApt #1R (SEQ ID NO: 3) and TLRApt #4F (SEQ ID NO: 4). By means of the same type of assay, aptamers TLRApt #2F and TLRApt #3R were identified. FIG. 2 shows the most likely sequences and secondary structures of the selected aptamers TLRApt #1R (SEQ ID NO: 3) and TLRApt #4F (SEQ ID NO: 4), obtained using mFold software (Zuker M., 2003, Nucleic Acids Res 31:3406-15).

Figure 3:
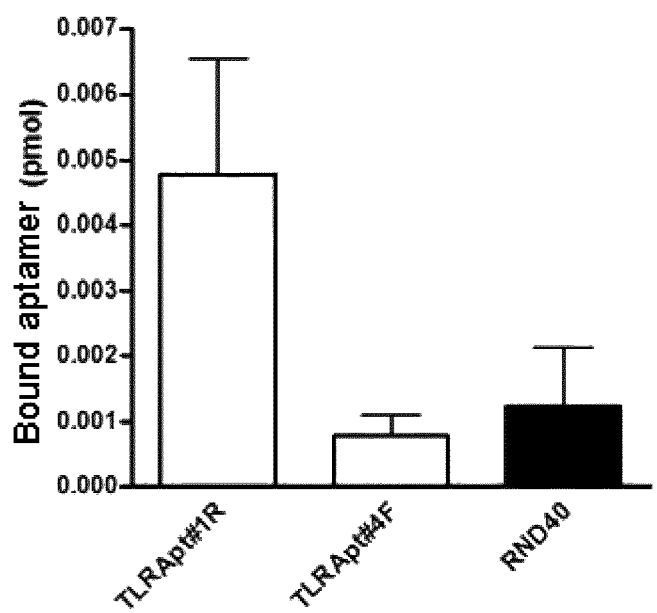
FIG. 3. Binding of aptamers TLRApt #1R (SEQ ID NO: 3) and TLRApt #4F (SEQ ID NO: 4) to recombinant hTLR-4 (A) and to the TLR-4 protein expressed in cells (B). All the experiments were done in triplicate.
Figure 3:
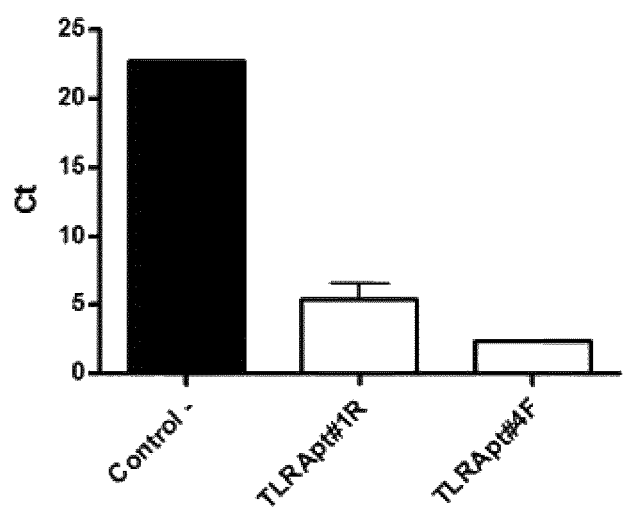

The capability of binding of the aptamers to hTLR-4 was determined by means of incubation of the aptamers with a Ni-NTA resin with bound hTLR-4, recovery and subsequent qPCR amplification of the bound aptamers. The obtained results show that all the selected aptamers are able to bind to the recombinant hTLR-4 protein (FIG. 3A). In these experiments, a lower Ct value indicates a larger amount of aptamer bound to hTLR-4.

For the purpose of analyzing the capability of the identified aptamers of binding to the TLR-4 protein expressed in HEK-293 cells, 20 pmol (500 ng) of aptamers TLRApt #1R (SEQ ID NO: 3) and TLRApt #4F (SEQ ID NO: 4) are added to a HEK-293-TLR4 cell culture. After incubating for 30 min at 37° C., 5% $CO_2$, the cells are washed and recovered, and qPCR is performed for the purpose of calculating the Ct values. In these experiments, a lower Ct value indicates a larger amount of aptamer bound to the cells. The obtained results show that the selected aptamers TLRApt #1R (SEQ ID NO: 3) and TLRApt #4F (SEQ ID NO: 4) (FIG. 3B) are those which bind with a higher affinity.

Figure 4:
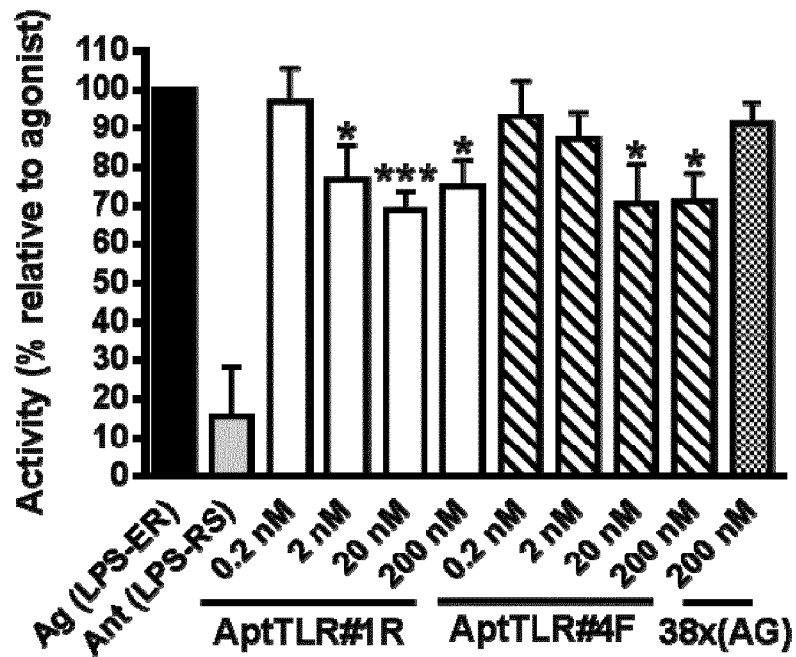
FIG. 4. Antagonist effect of aptamers TLRApt #1R (SEQ ID NO: 3) and TLRApt #4F (SEQ ID NO: 4) on HEK-Blue hTLR4 cells and antagonist LPS-RS-UP (2 ng/µl; 20 ng) as control. Aptamers were applied at end concentrations of 0.2, 2, 20 and 200 nM or the antagonist control LPS-RS-UP (2 ng/µl; 20 ng). The agonist LPS-EK-UP (0.02 ng/µl) (A) or lysates from HEK293 cells (Damage-associated molecular pattern; DAMP) (B) were used as agonist control and secreted alkaline phosphatase (SEAP) activity was measured after 24 h using QUANTI-Blue™ substrate at 630 nm. Data are expressed as the percentage of SEAP activity relative to the control cells. All the experiments were done in triplicate and average of 7-9 different experiments is shown in the figure. Statistical significance (*P<0.05, P<0.01 and *P<0.001).
Figure 4:
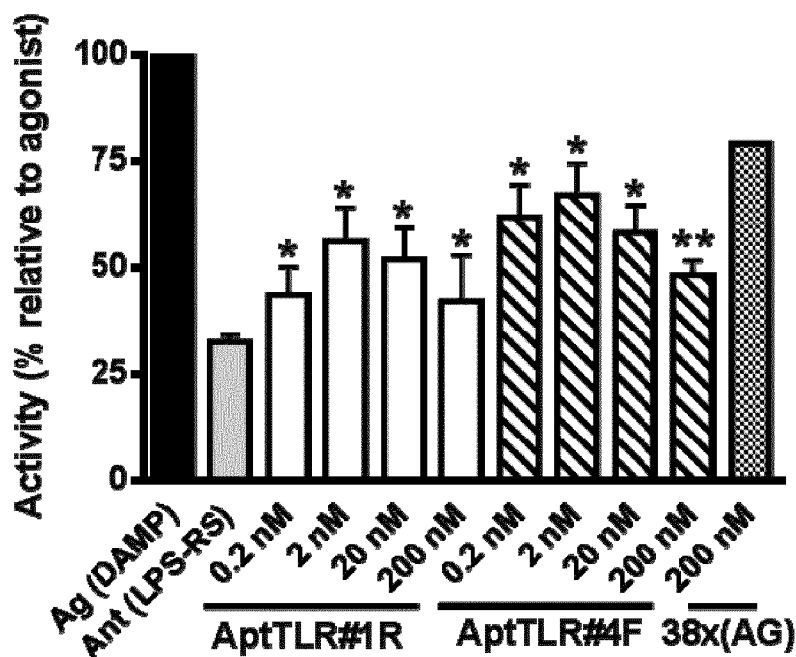

Dose-response curves were made for the purpose of determining the concentration of each aptamer at which the maximum antagonist effect is obtained using as agonist LPS-EK-UP (FIG. 4A) or lysates from HEK293 cells (Damage-associated molecular pattern; DAMP) (FIG. 4B). Based on the results obtained, it can be concluded that the concentrations at which the best effect is observed are 20 nM for agonist LPS-EK-UP and 200 nM for DAMPs.

Figure 5:
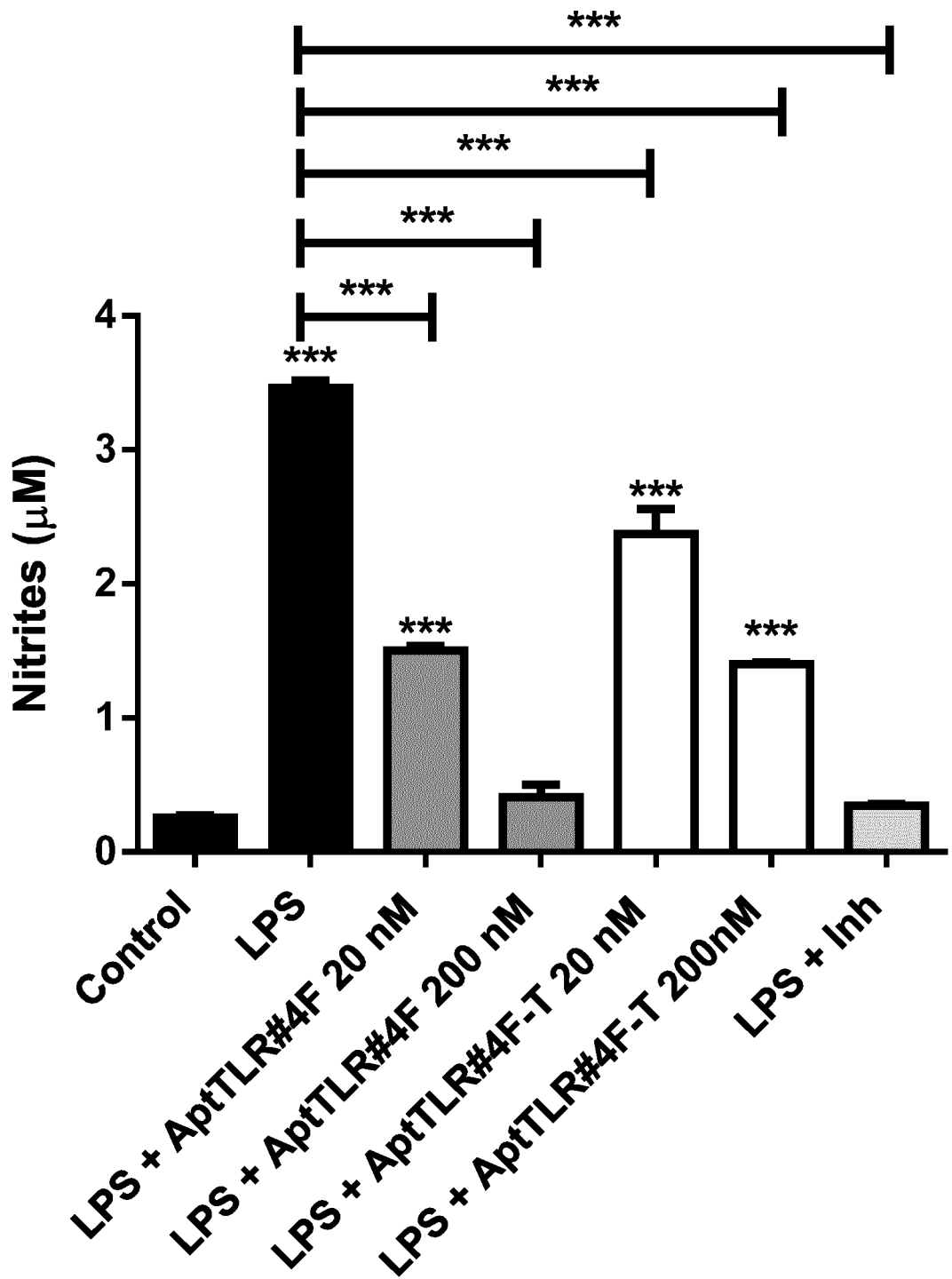
FIG. 5. Effect of aptamers TLRApt #4F-T (SEQ ID NO: 2) and TLRApt #4F (SEQ ID NO: 4) on macrophages stimulated in the presence of 500 ng/ml LPS. Nitrites release was studied by the Griess reaction at 24 h aptamer addiction. Samples were assayed in duplicate. The differences were analyzed by one-way ANOVA followed by Bonferroni test. The result is the average of three experiments tested in duplicate. Statistical significance (***P<0.001). Keys: 38× (AG) is the oligonucleotide of sequence SEQ ID NO: 7, which is a nonspecific sequence that is not able to adopt any secondary structure; lnh: hispanolone derivative compound 11 (Girón et al., 2008, Toxicol Appl Pharmacol 228:179-89).

The effect of the aptamers on macrophages is shown in FIG. 5. Aptamers TLRApt #4F (SEQ ID NO: 4) and TLRApt #4F-T (SEQ ID NO: 2) inhibited nitrite release after stimulation of macrophages with LPS. In these experiments, aptamer TLRApt #4F (SEQ ID NO: 4) seems more active than TLRApt #4F-T (SEQ ID NO: 2) for the same concentrations.

Example 3

Figure 6:
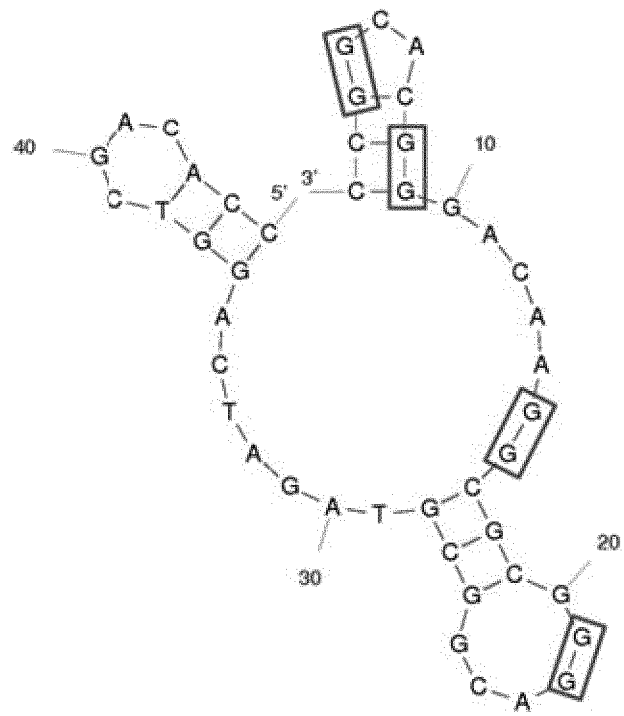
FIG. 6. Secondary structures of aptamers TLRApt #1R-T (SEQ ID NO: 1) and TLRApt #4F-T (SEQ ID NO: 2) predicted using the mFold program. The guanines that could be part of predicted G-quadruplex structures are shown in the boxes with the QGRS Mapper program.
Figure 6:
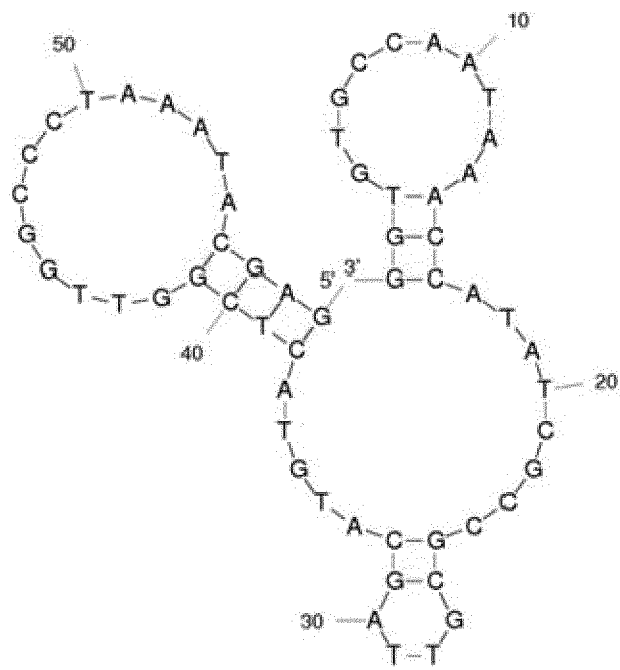

Optimization of the Aptamer Antagonists of TLR-4 for Increasing its Activity and Stability in Animal Models The aptamers that showed the capability of inhibiting receptor TLR-4 have been modified by means of removing specific regions from the sequence thereof for the purpose of increasing the stability and/or resistance with respect to nucleases. To that end, a study of the secondary structure of the different aptamers was conducted using the mFold program (Zuker M., 2003, mentioned at supra) and the capability of the aptamers of forming G-quadruplex structures has been analyzed by means of the QGRS Mapper program (Kikin et al., 2006, Nucleic Acids Res 34:W676-W682). Therefore, aptamers TLRApt #1R-T (SEQ ID NO: 1) and TLRApt #4F-T (SEQ ID NO: 2), corresponding to those identified in the first screenings (FIG. 6), were designed and synthesized.

Example 4

Effect of the Aptamer Antagonists of TLR-4 in an Animal Model of Stroke

The capability of the new aptamers, optimized for blocking the inflammatory response produced after an episode of stroke in an animal model of stroke, evaluating the capability of the aptamers specific for TLR-4 of reducing the cerebral injury.

Figure 7:
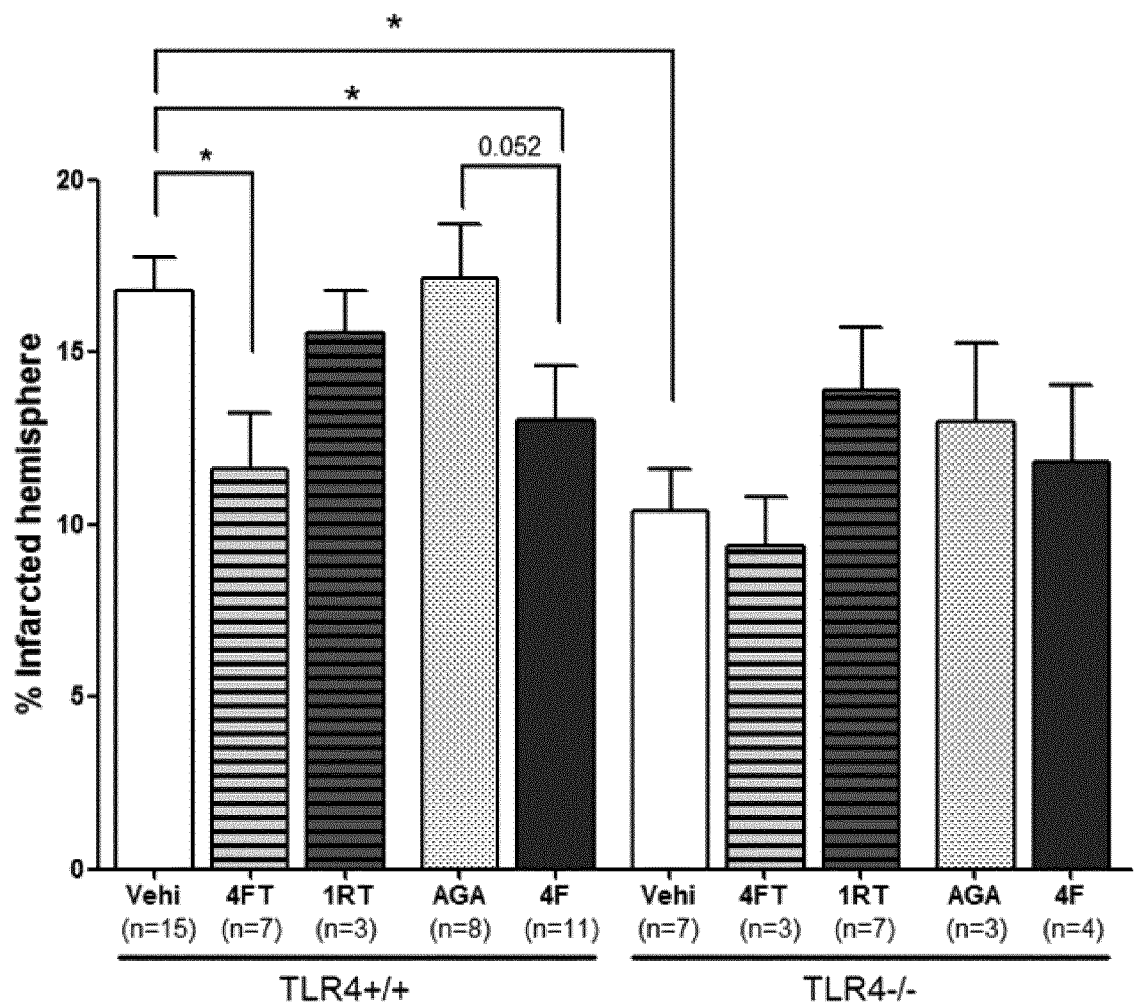
FIG. 7. Effect of the intraperitoneal injection of 1 nmol of aptamers TLRApt #1R-T (SEQ ID NO: 1), TLRApt #4F-T (SEQ ID NO: 2) and TLRApt #4F (SEQ ID NO: 4) or 38×(AG) (SEQ ID NO: 7) or vehicle (PBS+1 mM Mg$^{2+}$) in the reduction of the infarcted area in animals used in experiments. Adult male mice C57BL/10ScSn (WT; normal) and C57BL/10ScNJ (KO, lacking functional TLR4), were subjected to induction of a focal cerebral ischemia by means of occlusion of the middle cerebral artery via ligature. The mice were anesthetized with isoflurane and 24 hours after MCAO, the size of the infarction was evaluated by MRI. The images highlighted in T2 (T2W1) have been acquired in a BIOSPEC BMT 47/40 operating at 4.7 T (Bruker-Medical, Ettlingen, Germany; MRI Unit, Instituto Pluridisciplinar, UCM) and the damaged area is quantified by means of Image J 1.41 (NIH, Bethesda, Wash.). Statistical significance (*P<0.05). Keys: 1 RT, TLRApt #1R-T; 4FT, TLRApt #4F-T; 4F, TLRApt #4F.

To that end, adult male TLR-4-deficient mice (C57BL/10ScNJ) and control mice expressing TLR-4 (C57BL/10ScSn) were used, in which focal cerebral ischemia was induced by means of median cerebral arterial occlusion (MCAO). The results obtained in mice normally expressing TLR4 (control mice) demonstrate that the aptamers cause a reduction in size of the infarcted area which, in the case of aptamer TLRApt #4F-T (SEQ ID NO: 2), is statistically significant. In addition, the results obtained in TLR-4-deficient mice show that there is no effect of aptamer TLRApt #4F-T (SEQ ID NO: 2) on which it is obtained when the mice are treated with the vehicle (FIG. 7). This data clearly indicates that the effect of aptamer TLRApt #4F-T (SEQ ID NO: 2) occurs through TLR-4.

Figure 8:
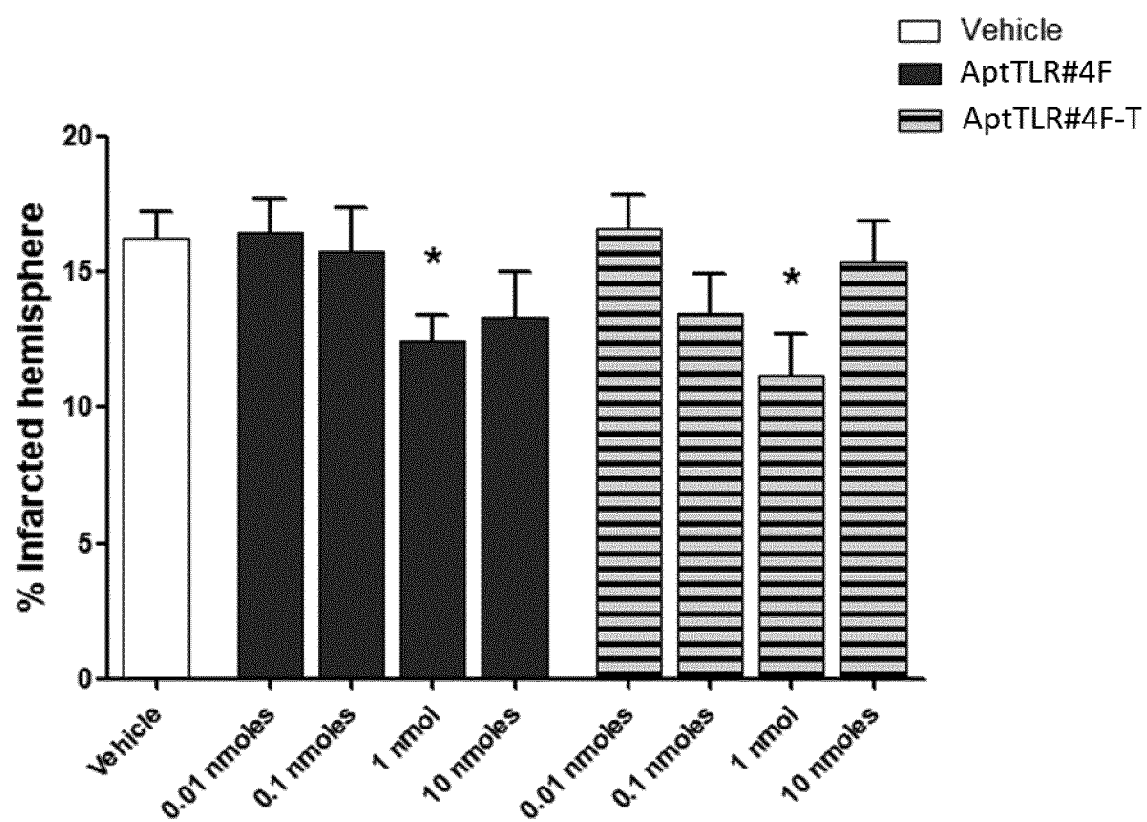
FIG. 8: Dose-response curve. Effect of the intraperitoneal injection of different amounts of aptamers TLRApt #4F-T (SEQ ID NO: 2) and TLRApt #4F (SEQ ID NO: 4) or vehicle (PBS+1 mM Mg2+) in the reduction of the infarcted area in animals used in experiments. Adult male mice C57BL/10ScSn (WT; normal were subjected to induction of a focal cerebral ischemia by means of occlusion of the middle cerebral artery via ligature. The mice were anesthetized with isoflurane and 24 hours after MCAO, the size of the infarction was evaluated by MRI. The images highlighted in T2 (T2W1) have been acquired in a BIOSPEC BMT 47/40 operating at 4.7 T (Bruker-Medical, Ettlingen, Germany; MRI Unit, Instituto Pluridisciplinar, UCM) and the damaged area is quantified by means of Image J 1.41 (NIH, Bethesda, Wash.). Statistical significance (*P<0.05).

In another set of experiments, adult male mice C57BL/10ScSn (WT; normal) were subjected to induction of a focal cerebral ischemia and then treated with intraperitoneal injection of different amounts of aptamers TLRApt #4F-T (SEQ ID NO: 2) and TLRApt #4F (SEQ ID NO: 4) or vehicle (PBS+1 mM $Mg^{2+}$). The results obtained demonstrate that the aptamers cause the higher reduction in size of the infarcted area at 1 nmol aptamer/animal and that this reduction is statistically significant (FIG. 8).

Example 5

Flow Cytometry

Figure 9:
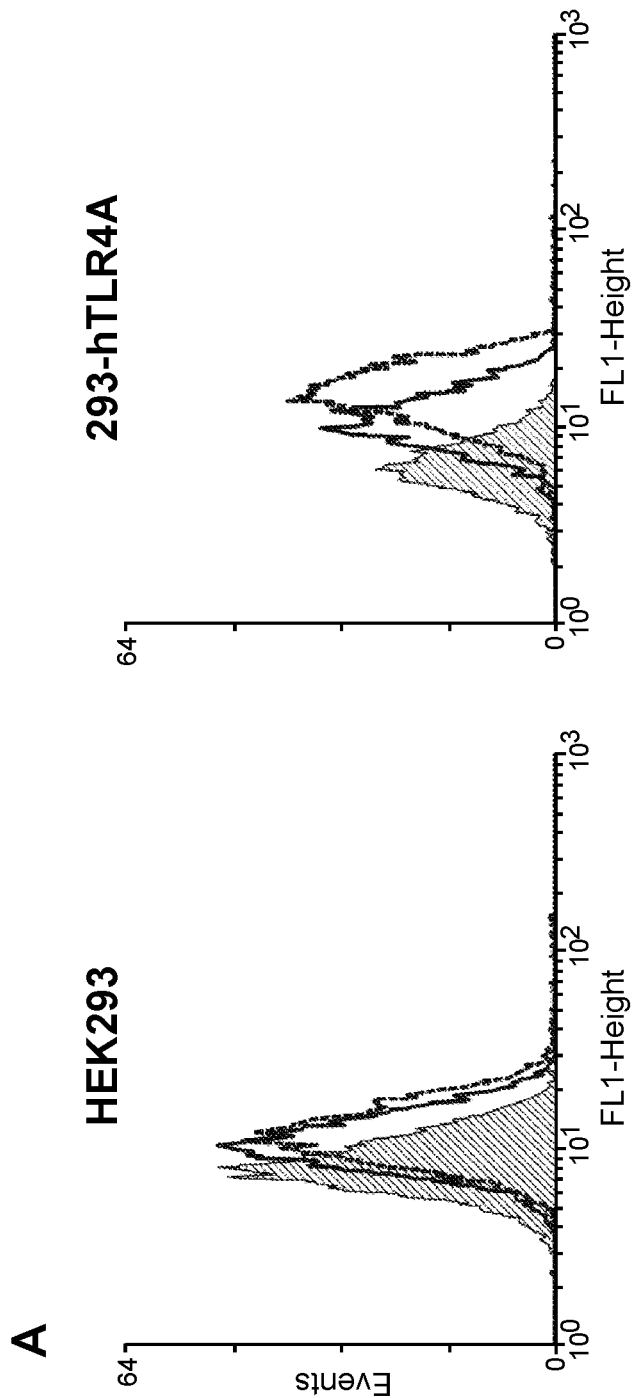
FIG. 9: Flow cytometry assays. (A) Human HEK293 (left panel) and 293-hTLR4A (right panel) cell lines were incubated with 20 nM Alexa fluor 488-labeled aptamers for 30 min at room temperature. The cells were washed with 2 ml of PBS and resuspended in 1 mL PBS for analysis. In each figure, the ordinate represents the frequency of events (or cell number) while the abscissa indicates the fluorescence intensity (FL1). Black area, autofluorescence; black line, aptamer TLRApt #1R-T (SEQ ID NO: 31); grey line, aptamer TLRApt #4F-T (SEQ ID NO: 42). (B) The human 293-hTLR4A cell line is activated with LPS-EK-UP and then incubated 30 min with 20 nM of Alexa Fluor 488-labeled aptamers for 30 min at room temperature. The cells are washed with 2 ml PBS and resuspended in 1 mL PBS for analysis. In each figure, the ordinate represents the frequency of events (or cell number) while the abscissa indicates the fluorescence intensity (FL1). Black area, autofluorescence; black line, aptamer TLRApt #1R-T (SEQ ID NO: 31); grey line, aptamer TLRApt #4F-T (SEQ ID NO: 42).
Figure 9:
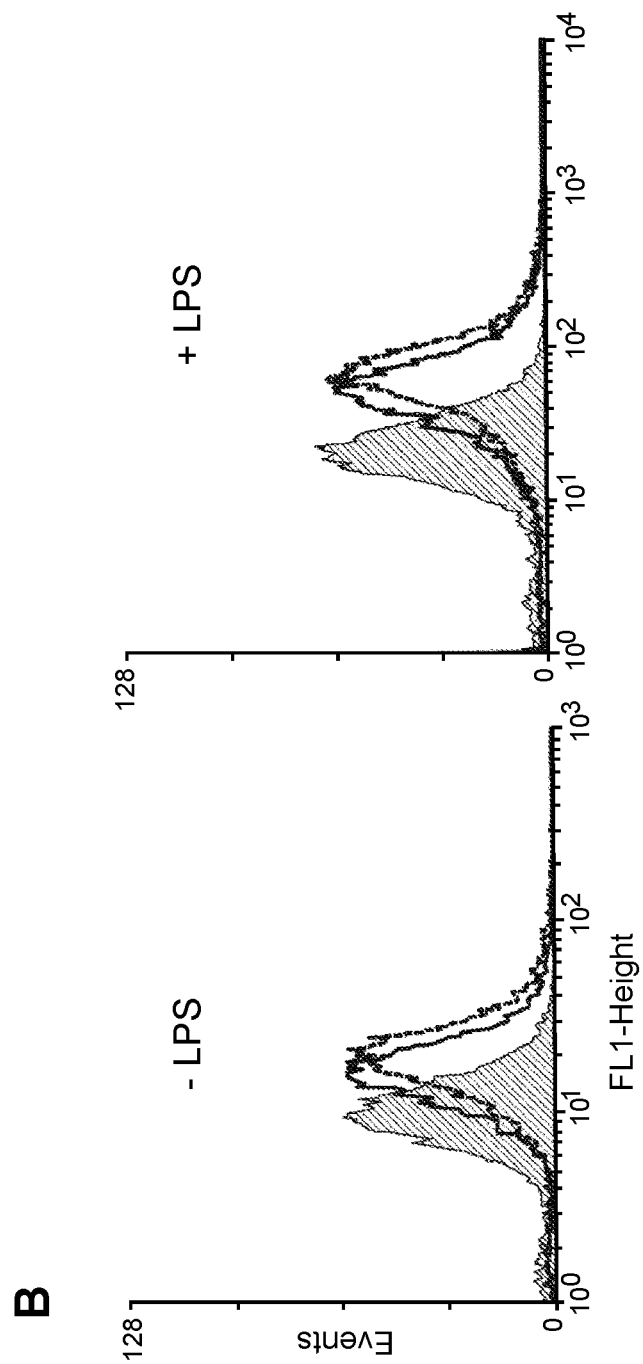

Flow cytometry assays were performed using HEK293 cell line transfected with human TLR4, 293-hTLR4A. The parental human HEK293 cell line, lacking human TLR4, was used as a control. In this experiment aptamers were labeled with Alexa Fluor 488. FIG. 9A shows that Alexa Fluor 488-labelled aptamers bind strongly to 293-hTLR4A cells (right panel), but not to HK293 cells lacking human TLR4 (left panel). In addition, it is observed that ApTLR #4F-T (SEQ ID NO: 2) binds to the target with higher affinity than ApTLR #1R-T (SEQ ID NO: 1). In turn, the results of cellular staining using the selected aptamers after activation (or not) of hTLR4-Blue-HEK cells were compared. As expected, aptamers bound TLR4 after activation in a similar level relative to non-activated cells (FIG. 9B).

Example 6

Half-Life Calculation by Nucleases Digestion

Figure 10:
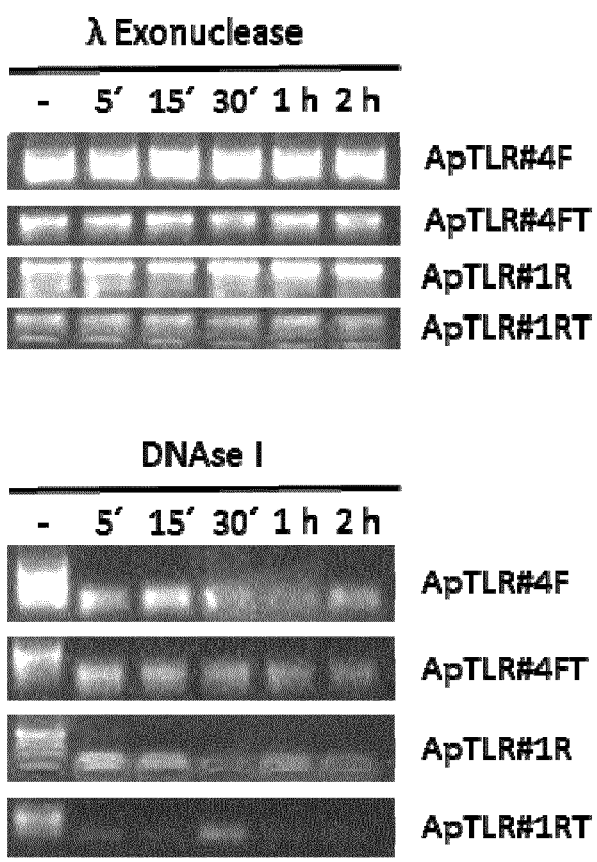
FIG. 10: Analysis of the half-life of the aptamers in vitro. Three hundred ng of folded aptamers were incubated with 2 units of λ Exonuclease or DNAse I for several periods of time at 37° C. Afterward, samples were solved on a 3% agarose gel and bands visualized by GelRed and quantified using Image Studio Digits V3.1 software.

The half-life of the aptamers was measured in vitro in the presence of λ Exonuclease or DNAse I (FIG. 10). Results show that the four aptamers are resistant to λ Exonuclease meanwhile DNAse I produces a time-dependent degradation of the four aptamers. Thus, aptamer ApTLR #1R-T (SEQ ID NO: 1) is the most sensible and is completely degraded after 5 min incubation in presence of DNAse I. On the contrary, aptamers ApTLR #4F (SEQ ID NO: 4) and ApTLR #4F-T (SEQ ID NO: 2) are resistant even after 2 h incubation with DNAse I.

CONCLUSIONS

Aptamers TLRApt #1R (SEQ ID NO: 3) and TLRApt #4F (SEQ ID NO: 4) have been selected with respect to the extracellular domain of receptor TLR-4, which recognize human receptor TLR-4, both in its soluble recombinant form (in vitro) and integrated in the membrane of HEK293 cells (in vivo).

Aptamers TLRApt #1R (SEQ ID NO: 3) and TLRApt #4F (SEQ ID NO: 4) show an antagonist effect of receptor TLR-4.

Aptamers TLRApt #1R-T (SEQ ID NO: 1) and TLRApt #4F-T (SEQ ID NO: 2) have been obtained in truncated form maintaining the antagonist activity of the original aptamers TLRApt #1R (SEQ ID NO: 3) and TLRApt #4F (SEQ ID NO: 4), respectively.

Aptamer TLRApt #4F-T (SEQ ID NO: 2) is able to reduce the infarcted area in an animal model of stroke.

Aptamers TLRApt #1R (SEQ ID NO: 3) y TLRApt #4F (SEQ ID NO: 4), selected against the extracellular domain of TLR4 receptor, recognize the human TLR-4 receptor in both its recombinant soluble form (in vitro), as integrated in the membrane of HEK293 cells (in vivo).

---

The invention claimed is:

1. A method to improve one of more symptom of the pathology of multiple sclerosis in a subject in need thereof comprising administering to the subject an effective amount of an active compound comprising at least one nucleic acid aptamer or chemically modified variant thereof, wherein said at least one nucleic acid aptamer or chemically modified variant thereof specifically binds to at least one target site on the extracellular domain of human TLR-4 (Toll-like receptor 4) on at least one target cell, wherein
   (i) the specific binding of the at least one nucleic acid aptamer or chemically modified variant thereof to the extracellular domain of human TLR-4 results in a decrease in TLR-4 activity; and
   (ii) the decrease in TLR-4 activity improves one of more symptoms of the pathology of multiple sclerosis in the subject,
wherein the at least one nucleic acid aptamer or chemically modified variant thereof comprises a sequence at least 70% identical to SEQ ID NO: 1, SEQ ID NO: 2, SEQ ID NO: 3 or SEQ ID NO: 4, or a combination thereof.

2. The method of claim 1, wherein the at least one nucleic acid aptamer or chemically modified variant thereof comprises
   (a) 1, 2, 3, 4, 5, 10, 15, or 20 additional nucleotides at the 5' end of the sequence of SEQ ID NO: 1 or SEQ ID NO: 2;
   (b) 1, 2, 3, 4, 5, 10, 15, or 20 additional nucleotides at the 3' end of the sequence of SEQ ID NO: 1 or SEQ ID NO: 2; or,
   (c) a combination thereof.

3. The method of claim 1, wherein the at least one nucleic acid aptamer sequence is selected from the group consisting of SEQ ID NO: 1, SEQ ID NO: 2, SEQ ID NO: 3 and SEQ ID NO: 4, or a combination thereof.

4. The method of claim 1, wherein the target site can specifically bind to at least one nucleic acid aptamer of SEQ ID NO: 1, SEQ ID NO: 2, SEQ ID NO: 3 or SEQ ID NO:4, or a combination thereof.

5. The method of claim 1, wherein the subject is a human.

6. The method of claim 1, wherein the active compound comprises a complex.

7. The method of claim 1, wherein the active compound comprises a conjugate.

8. The method of claim 1, wherein the active compound further comprises a functional group comprising a drug, a nanoparticle, or a combination thereof.

9. The method of claim 8, wherein the drug comprises a TLR-4 antagonist, an anti-inflammatory agent, a nucleic acid, a peptide, or a combination thereof.

10. The method of claim 8, wherein the nanoparticle comprises a polymeric nanoparticle, a lipid nanoparticle, a metal nanoparticle, or a combination thereof.

11. The method of claim 10, wherein the metal is selected from the group consisting of gold, silver, copper, aluminum, platinum, iron, cobalt, palladium, and combinations thereof.

12. The method of claim 1, wherein the at least one nucleic acid aptamer or chemically modified variant thereof comprises at least one nucleic acid analogue.

13. The method of claim 1, wherein the decrease in TLR-4 activity results in a reduction and/or interruption in the release of at least one pro-inflammatory cytokine.

14. The method of claim 13, wherein the at least one inflammatory cytokine is selected from the group consisting of IL-1, IL-8, TNF-alpha, IL-12, and combinations thereof.

15. The method of claim 1, wherein the one of more symptom of the pathology of multiple sclerosis is selected from:
   (i) demyelination;
   (ii) neurodegenerative lesions of the central nervous system;
   (iii) chronic lesions of the central nervous system;
   (iv) TLR-4-expressing cells crossing the blood barrier;
   (v) inflammatory processes aided by TLR-4-expressing cells; and,
   (vi) a combination thereof.

16. The method of claim 15, wherein the TLR-4 expressing cells comprise:
   (i) lymphoid lineage cells;
   (ii) myeloid lineage cells;
   (iii) neurons;
   (iv) neuroglia cells; or,
   (v) combinations thereof.

17. The method of claim 16, wherein the lymphoid lineage cells comprise lymphocytes.

18. The method of claim 16, wherein the myeloid lineage cells comprise monocytes, macrophages, microglia cells, granulocytes, dendritic cells, or combinations thereof.

19. The method of claim 1, wherein the decrease in TLR-4 activity prolongs the survival of the subject.

20. The method of claim 1, wherein the active compound is administered parenterally.

21. The method of claim 1, wherein the active compound is administered intravenously, intraperitoneally, intramuscularly, or subcutaneously.

22. The method of claim 1, wherein the active compound is administered one time or more than one time a day.

23. The method of claim 1, wherein the at least one target cell comprises a myeloid lineage cell, a neuron, or a combination thereof.

24. A method for imaging TLR-4 in vivo in a subject with multiple sclerosis comprising (i) administering to the subject an active compound comprising at least one nucleic acid aptamer or chemically modified variant thereof, wherein the at least one nucleic acid aptamer or chemically modified variant thereof specifically binds to at least one target site on the extracellular domain of human TLR-4 on the surface of at least one target cell in said subject; and, (ii) detecting the binding of said at least one nucleic acid aptamer or chemically variant thereof to target cells which express TLR4 in said subject,
   wherein the at least one nucleic acid aptamer or chemically modified variant thereof comprises a nucleic acid sequence at least 70% identical to SEQ ID NO: 1, SEQ ID NO: 2, SEQ ID NO:3 or SEQ ID NO: 4, or a combination thereof.

25. The method of claim 24, wherein the at least one nucleic acid aptamer or chemically modified variant thereof comprises a nucleic acid sequence selected from the group consisting of SEQ ID NO: 1, SEQ ID NO: 2, SEQ ID NO:3 or SEQ ID NO: 4, or a combination thereof.

26. The method of claim 24, wherein the active compound further comprises a detectable moiety.

27. The method of claim 26, wherein the detectable moiety is covalently bound to the active compound.

28. The method of claim 26, wherein the detectable moiety comprises a radionuclide, a fluorophore, a contrast media, a protein, a haptene, or a combination thereof.

29. The method of claim 24, wherein the active compound is detected by a detectable reagent.

30. The method of claim 29, wherein the detectable reagent comprises a radionuclide, a fluorophore, a contrast media, a protein, a haptene, or a combination thereof.

* * * * *

SEQUENCE LISTING

```
<160> NUMBER OF SEQ ID NOS: 7

<210> SEQ ID NO 1
<211> LENGTH: 45
<212> TYPE: DNA
<213> ORGANISM: Artificial Sequence
<220> FEATURE:
<223> OTHER INFORMATION: TLRApt#1R-T aptamer with the capability of
      binding specifically to and inhibiting TLR-4

<400> SEQUENCE: 1
ccggcacggg acaaggcgcg ggacggcgta gatcaggtcg acacc              45

<210> SEQ ID NO 2
<211> LENGTH: 59
<212> TYPE: DNA
<213> ORGANISM: Artificial Sequence
<220> FEATURE:
<223> OTHER INFORMATION: TLRApt#4F-T aptamer with the capability of
      binding specifically to and inhibiting TLR-4

<400> SEQUENCE: 2
ggtgtgccaa taaaccatat cgccgcgtta gcatgtactc ggttggccct aaatacgag    59

<210> SEQ ID NO 3
<211> LENGTH: 78
<212> TYPE: DNA
<213> ORGANISM: Artificial Sequence
<220> FEATURE:
<223> OTHER INFORMATION: TLRApt#1R aptamer with the capability of
      binding specifically to and inhibiting TLR-4

<400> SEQUENCE: 3
gttgctcgta tttagggcca ccggcacggg acaaggcgcg ggacggcgta gatcaggtcg    60
acaccagtct tcatccgc                                                 78
```

```
<210> SEQ ID NO 4
<211> LENGTH: 76
<212> TYPE: DNA
<213> ORGANISM: Artificial Sequence
<220> FEATURE:
<223> OTHER INFORMATION: TLRApt#4F aptamer with the capability of
      binding specifically to and inhibiting TLR-4

<400> SEQUENCE: 4
gcggatgaag actggtgtgc caataaacca tatcgccgcg ttagcatgta ctcggttggc    60
cctaaatacg agcaac                                                    76

<210> SEQ ID NO 5
<211> LENGTH: 18
<212> TYPE: DNA
<213> ORGANISM: Artificial Sequence
<220> FEATURE:
<223> OTHER INFORMATION: Primer for amplifying aptamers

<400> SEQUENCE: 5
gcggatgaag actggtgt                                                  18

<210> SEQ ID NO 6
<211> LENGTH: 18
<212> TYPE: DNA
<213> ORGANISM: Artificial Sequence
<220> FEATURE:
<223> OTHER INFORMATION: Primer for amplifying aptamers

<400> SEQUENCE: 6
gttgctcgta tttagggc                                                  18

<210> SEQ ID NO 7
<211> LENGTH: 76
<212> TYPE: DNA
<213> ORGANISM: Artificial Sequence
<220> FEATURE:
<223> OTHER INFORMATION: Nonspecific sequence that is not able to adopt
      any secondary structure

<400> SEQUENCE: 7
agagagagag agagagagag agagagagag agagagagag agagagagag agagagagag    60
agagagagag agagag                                                    76
```